United States Patent [19]

Sohda et al.

[11] Patent Number: 5,641,788

[45] Date of Patent: Jun. 24, 1997

[54] QUINOLINE DERIVATIVES AND PHARMACEUTICAL COMPOSITION CONTAINING THEM

[75] Inventors: Takashi Sohda, Osaka; Haruhiko Makino; Atsuo Baba, both of Hyogo, all of Japan

[73] Assignee: Takeda Chemical Industries, Ltd., Osaka, Japan

[21] Appl. No.: 460,776

[22] Filed: Jun. 2, 1995

[30] Foreign Application Priority Data

Jun. 7, 1994 [JP] Japan ................................. 6-125022

[51] Int. Cl.$^6$ ...................... A61K 31/47; C07D 215/60; C07D 215/14
[52] U.S. Cl. ...................... 514/312; 514/311; 546/153; 546/156; 546/168; 546/180
[58] Field of Search ...................... 546/153, 156, 546/168, 180; 514/312, 313, 311

[56] References Cited

FOREIGN PATENT DOCUMENTS

| | | |
|---|---|---|
| 0567107 | 10/1993 | European Pat. Off. . |
| 0608870 | 8/1994 | European Pat. Off. . |
| 0634169 | 1/1995 | European Pat. Off. . |
| 2134169 | 8/1972 | France . |

OTHER PUBLICATIONS

Walser et al., "Nucleophilic Displacement of Aromatic Fluorine. Part IV. Quinolinoquinolines and Benzochromenoquinolines," *J. Heterocyclic Chem.*, vol. 12(4), pp. 737–741, (1975).

Fehnel et al., "Friedlander Syntheses With o–Aminoaryl Ketones. II. Structure of the Product Formed IN the Condensation of o–Aminobenzophenone With Acetylacetone", *J.O.C.*, vol. 31(11), pp. 3852–3854, (1966).

Chemical Abstracts, vol. 79:348, (1973), p. 348.

Partial English Translation of Nippon Kagaku Zasshi, vol. 99(1), pp. 81–85, (1969).

Synthesis International Journal of Methods in Synthetic Organic Chemistry, No. 9, pp. 718–719, (1979).

Anzini et al., "Synthesis And 5HT–Receptors Affinity Of Some 4–Phenylquinoline Derivatives", *IL Farmaco*, vol. 44(6), pp. 555–563, (1989).

*Primary Examiner*—C. Warren Ivy
*Assistant Examiner*—D. Margaret M. Mach
*Attorney, Agent, or Firm*—Foley & Lardner

[57] ABSTRACT

The present invention provides a novel quinoline derivative useful as an anti-inflammatory agent, particularly an agent for treating arthritis, or a salt thereof. The present invention also provides a composition, particularly an anti-inflammatory composition for pharmaceutical use, comprising the novel quinoline compound of formula (I):

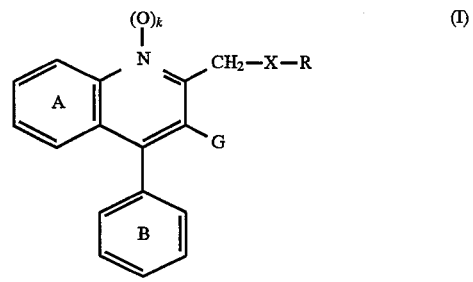

wherein

G is an acyl group, optionally protected hydroxyalkyl group, amidated carboxyl group or halogen atom;

X is an oxygen atom, optionally oxidized sulfur atom or —$(CH_2)_q$— in which q is an integer of 0 to 5;

R is an optionally substituted amino group or optionally substituted heterocyclic group;

each of the ring A and ring B may optionally be substituted; and k is 0 or 1.

25 Claims, No Drawings

QUINOLINE DERIVATIVES AND PHARMACEUTICAL COMPOSITION CONTAINING THEM

FIELD OF THE INVENTION

The present invention relates to a novel quinoline derivative useful as an anti-inflammatory agent, particularly an agent for treating arthritis, or a salt thereof. The present invention also relates to a pharmaceutical composition containing the novel quinoline compound.

BACKGROUND OF THE INVENTION

Arthritis is an inflammatory disease of arthroses. Main examples of arthritis are rheumatoid arthritis and its analogous diseases wherein inflammation is observed in arthroses.

In particular, rheumatoid arthritis, also referred to as chronic rheumatism, is polyarthritis chronica whose main lesion is inflammatory changes in synovial membranes of internal layers of articular capsules. Arthritis such as rheumatoid arthritis is progressive and causes articular disorders such as articular deformation, tetany, etc. When an effective treatment is not carried out and the disease worsens, serious physical disorders are often caused.

Hitherto, in treatment of such arthritis, chemotherapy has been carried out using steroids such as adrenal cortical hormones (e.g., cortisone, etc.), etc.; non-steroidal anti-inflammatory agents such as aspirin, piroxicam, indomethacin, etc.; gold preparations such as gold thiomalate, etc.; antirheumatic agents such as chloroquine preparations, D-penicillamine, etc.; antipodagrics such as colchicine, etc.; immunosuppressive agents such as cyclophosphamide, azathioprine, methotrexate, levamisole, etc.

However, these drugs have problems such as serious side effects, side effects making their long-term use difficult, insufficient efficacy, inefficacy against arthritis which has already produced the symptoms.

Therefore, in clinical treatment of arthritis, drugs having low toxicity and excellent effects in the prophylaxis and treatment of arthritis have been required.

Various quinoline derivatives having an acyl group, hydroxyalkyl group or amidated carboxyl group at the 3-position have been synthesized. For example, Journal of Heterocyclic Chemistry, Vol. 12, p. 737 (1975) discloses 4-phenylquinoline derivatives having a hydroxymethyl group or amidated carboxyl group at the 3-position. The Journal of Organic Chemistry, Vol. 31, p. 3852 (1966) and Nippon Kagaku Zasshi, Vol. 90, p. 81 (1969) disclose 4-phenylquinoline derivatives having an acetyl group at the 3-position. Further, Chemical Abstracts, Vol. 79, 42371h (1973) discloses anti-inflammatory activity of 3-acylquinoline derivatives. The substituents at the 2-position of the compounds disclosed in these literature are, however, limited to an alkyl group, phenyl group, etc.

OBJECTS OF THE INVENTION

The main object of the present invention is to provide a novel quinoline derivative having anti-inflammatory activity.

Another object of the present invention is to provide a pharmaceutical composition, particularly an anti-inflammatory composition, containing a quinoline derivative.

These objects as well as other objects and advantages of the present invention will become apparent to those skilled in the art from the following description.

SUMMARY OF THE INVENTION

The present inventors have found that novel 4-phenylquinoline derivatives which contain at the 2-position an alkylene group having an optionally substituted amino group or optionally substituted heterocyclic group, and at the 3-position an acyl group, a halogen atom, a hydroxyalkyl group or an amidated carboxyl group have anti-inflammatory activity, and are useful as an agent for inhibiting arthral destruction. Thus, the present invention has been completed.

The present invention provides:

(1) a compound of the formula (I'):

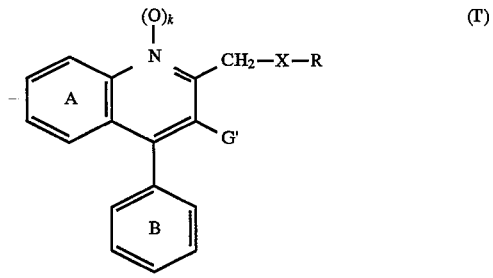

wherein

G' is an acyl group, optionally protected hydroxyalkyl group having not less than 2 carbon atoms, or halogen atom;

X is an oxygen atom, optionally oxidized sulfur atom or $-(CH_2)_q-$ in which q is an integer of 0 to 5;

R is an optionally substituted amino group or optionally substituted heterocyclic group;

each of the ring A and ring B may optionally be substituted; and k is 0 or 1;

or a salt thereof, (2) the compound of the above item (1), wherein X is $-(CH_2)_q-$ in which q is 0 or 1, or salt thereof, (3) the compound of the above item (1), wherein R is an optionally substituted amino group, or a salt thereof, (4) the compound of the above item (3), wherein the substituent of the optionally substituted amino group represented by R is an optionally substituted alkyl group, or a salt thereof, (5) the compound of the above item (1), wherein the optionally substituted heterocyclic group represented by R is an aromatic 5-membered heterocyclic group containing 2 to 3 heteroatoms, or a salt thereof, (6) the compound of the above item (1), wherein the optionally substituted heterocyclic group represented by R is a 5- to 7-membered heterocyclic group containing one sulfur atom, nitrogen atom or oxygen atom, a 5- to 6-membered heterocyclic group containing 2 to 4 nitrogen atoms or a 5- to 6-membered heterocyclic group containing 1 to 2 nitrogen atoms and one sulfur atom or oxygen atom, each of which may optionally be substituted, or a salt thereof, (7) the compound of the above item (1), wherein X is a thio group, sulfinyl group or sulfonyl group, or a salt thereof, (8) the compound of the above item (1), wherein G' is an acyl group, or a salt thereof, (9) the compound of the above item (8), wherein G' is an acetyl group, or a salt thereof,

(10) the compound of the above item (1), wherein the ring A is substituted with at least one alkoxy group, or a salt thereof,

(11) the compound of the above item (10), wherein the ring A is substituted with the same or different two alkoxy groups, or a salt thereof,

(12) the compound of the above item (11), wherein the ring A is substituted with two alkoxy groups at the 6- and 7-positions of the quinoline ring, or a salt thereof,

(13) the compound of the above item (1), wherein the ring B is substituted with at least one alkoxy group, or a salt thereof,

(14) the compound of the above item (13), wherein the ring B is substituted with the same or different two alkoxy groups, or a salt thereof,

(15) the compound of the above item (14), wherein the ring B is substituted with two alkoxy groups at the 3- and 4- positions, or a salt thereof,

(16) the compound of the above item (1), wherein k is 0, or a salt thereof,

(17) the compound of the above item (1), which is 3-acetyl-2-(N,N-diethylaminomethyl)-4-(3,4-dimethoxy-phenyl)-6,7-dimethoxyquinoline, or a salt thereof,

(18) a pharmaceutical composition comprising a compound of the formula (I):

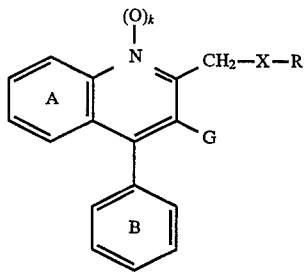

wherein

G is an acyl group, optionally protected hydroxyalkyl group, amidated carboxyl group or halogen atom;

X is an oxygen atom, optionally oxidized sulfur atom or —$(CH_2)_q$— in which q is an integer of 0 to 5;

R is an optionally substituted amino group or optionally substituted heterocyclic group;

each of the ring A and ring B may optionally be substituted; and k is 0 or 1;

or a pharmaceutically acceptable salt thereof, and a pharmaceutically acceptable carrier,

(19) an anti-inflammatory composition for pharmaceutical use, which comprises a compound of the formula

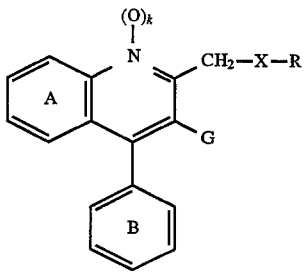

wherein

G is an acyl group, optionally protected hydroxyalkyl group, amidated carboxyl group or halogen atom;

X is an oxygen atom, optionally oxidized sulfur atom or —$(CH_2)_q$— in which q is an integer of 0 to 5;

R is an optionally substituted amino group or optionally substituted heterocyclic group;

each of the ring A and ring B may optionally be substituted; and k is 0 or 1;

or a pharmaceutically acceptable salt thereof, and a pharmaceutically acceptable carrier,

(20) a method of treating an inflammatory disease in a mammal which comprises administering to such mammal in need thereof an effective amount of a compound of the formula (I) or a salt thereof,

(21) the method of the above item (20), wherein the inflammatory disease is arthritis, and

(22) use of a compound of the formula (I) or a salt thereof in the manufacture of anti-inflammatory compositions for pharmaceutical use.

DETAILED DESCRIPTION OF THE INVENTION

The definitions of the symbols in the above formulas and their preferred examples are described below.

The optionally substituted amino group represented by R in the above formulas (I') and (I) is represented by the formula: —$N(R^1)(R^2)$ in which $R^1$ and $R^2$ are the same or different and are a hydrogen atom, optionally substituted hydrocarbon group or optionally substituted heterocyclic group.

The hydrocarbon group of the optionally substituted hydrocarbon group represented by $R^1$ or $R^2$ includes aliphatic hydrocarbon groups, alicyclic hydrocarbon groups, alicyclic-aliphatic hydrocarbon groups, (aromatic carbocycle)-aliphatic hydrocarbon groups, aromatic hydrocarbon groups and the like.

Examples of such aliphatic hydrocarbon groups include saturated aliphatic hydrocarbon groups (e.g., alkyl groups) having 1 to 8 carbon atoms such as methyl, ethyl, propyl, isopropyl, butyl, isobutyl, sec-butyl, tert-butyl, pentyl, isopentyl, neopentyl, tert-pentyl, hexyl, isohexyl, heptyl, octyl and the like; unsaturated aliphatic hydrocarbon groups (e.g., alkenyl groups, alkynyl groups) having 2 to 8 carbon atoms, such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl and the like. In particular, ethyl, tert-butyl, etc. are preferred.

Examples of such alicyclic hydrocarbon groups include saturated alicyclic hydrocarbon groups (e.g., cycloalkyl groups) having 3 to 7 carbon atoms such as cyclopropyl, cyclobutyl, cyclopentyl, cyclohexyl, cycloheptyl and the like; and unsaturated alicyclic hydrocarbon groups (e.g., cycloalkenyl groups) having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl and the like.

Examples of such alicyclic-aliphatic hydrocarbon groups include those having 4 to 9 carbon atoms each of which is composed of the above alicyclic hydrocarbon group and aliphatic hydrocarbon group, such as cycloalkyl-alkyl groups, cycloalkenyl-alkyl groups, etc. Specific examples of the alicyclic-aliphatic hydrocarbon groups include cyclopropyl-methyl, cyclopropylethyl, cyclobutylmethyl, cyclopentylmethyl, 2-cyclopentenylmethyl, 3-cyclopentenylmethyl, cyclohexyl-methyl, 2-cyclohexenylmethyl, 3-cyclohexenylmethyl, cyclohexylethyl, cyclohexylpropyl, cycloheptylmethyl, cycloheptylethyl and the like.

Examples of such (aromatic carbocycle)-aliphatic hydrocarbon groups include phenylalkyl having 7 to 9 carbon atoms such as benzyl, phenethyl, 1-phenylethyl, 3-phenylpropyl, 2-phenylpropyl, 1-phenylpropyl and the like; naphthylalkyl having 11 to 13 carbon atoms such as α-naphthylmethyl, α-naphtylethyl, β-naphthylmethyl, β-naphthylethyl and the like.

Examples of such aromatic hydrocarbon groups include phenyl, naphthyl (e.g., α-naphthyl, β-naphthyl) and the like.

The heterocyclic group of the optionally substituted heterocyclic group represented by $R^1$ or $R^2$ includes 5- to 7-membered heterocyclic groups containing one sulfur atom, nitrogen atom or oxygen atom; 5- to 6-membered heterocyclic groups containing 2 to 4 nitrogen atoms; 5- to 6-membered heterocyclic groups containing 1 to 2 nitrogen atoms, and one sulfur atom or oxygen atom. Each of these heterocyclic groups may form a condensed ring with a 6-membered ring containing up to 2 nitrogen atoms, benzene ring or 5-membered ring containing one sulfur atom.

Specific examples of the heterocyclic group include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.; aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo-[1,2-a]pyridyl, imidazo[1,5-a]pyridyl, imidazo[1,2-b]-pyridazinyl, imidazo[1,2-a]pyrimidinyl, 1,2,4-triazolo[4,3-a]pyridyl, 1,2,4-triazolo[4,3-b]pyridazinyl, etc.; non-aromatic heterocyclic groups such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.

$R^1$ and $R^2$ may be linked together with the nitrogen atom to which they are attached to form a ring. Examples of such —N($R^1$)($R^2$) include 1-pyrrolidinyl, 1-imidazolidinyl, 1-imidazolyl, 1-pyrazolidinyl, 1-piperidyl (also mentioned as piperidino), 1-piperazinyl, 4-morpholinyl (also mentioned as morpholino), 4-thiomorpholinyl, homopiperazin-1-yl, pyrazol-1-yl, imidazol-1-yl, 1,2,3-triazol-1-yl, 1,2,4-triazol-1-yl, 1,2,3-triazol-2-yl, tetrazol-1-yl, benzimidazol-1-yl, indol-1-yl, 1H-indazol-1-yl, etc.

Each of the hydrocarbon groups and heterocyclic groups represented by $R^1$ or $R^2$ may be unsubstituted or substituted with 1 to 3 substituents at any possible position.

The substituents of the hydrocarbon groups or heterocyclic groups represented by $R^1$ or $R^2$ include, for example, aliphatic chain hydrocarbon groups, alicyclic hydrocarbon groups, aryl groups, aromatic heterocyclic groups, non-aromatic heterocyclic groups, halogen atoms, a nitro group, an optionally substituted amino group, optionally substituted acyl groups, an optionally substituted hydroxyl group, an optionally substituted thiol group, an optionally esterified carboxyl group and the like.

The aliphatic chain hydrocarbon group as the substituent of the hydrocarbon group or heterocyclic group represented by $R^1$ or $R^2$ include, for example, straight chain or branched aliphatic hydrocarbon groups such as alkyl groups, preferably alkyl groups having 1 to 10 carbon atoms; alkenyl groups, preferably alkenyl groups having 2 to 10 carbon atoms; alkynyl groups, preferably alkynyl groups having 2 to 10 carbon atoms and the like.

Preferred examples of the alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, decyl and the like.

Preferred examples of the alkenyl group include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Preferred examples of the alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

The alicyclic hydrocarbon group as the substituent of the hydrocarbon group or heterocyclic group represented by $R^1$ or $R^2$ include, for example, saturated or unsaturated alicyclic hydrocarbon groups such as cycloalkyl groups, cycloalkenyl groups, cycloalkadienyl groups and the like.

Preferred examples of the cycloalkyl groups include those having 3 to 10 carbon atoms such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]-octyl, bicyclo[3.2.2]nonyl, bicyclo[3.3.1]nonyl, bicyclo-[4.2.1]nonyl, bicyclo[4.3.1]decyl and the like.

Preferred examples of the cycloalkenyl groups include those having 3 to 7 carbon atoms such as 2-cyclopenten-1-yl, 3-cyclopenten-1-yl, 2-cyclohexen-1-yl, 3-cyclohexen-1-yl and the like.

Preferred examples of the cycloalkadienyl groups include those having 5 to 8 carbon atoms such as 2,4-cyclopentadien-1-yl, 2,4-cyclohexadien-1-yl, 2,5-cyclohexadien-1-yl and the like.

The aryl group as the substituent of the hydrocarbon group or heterocyclic group represented by $R^1$ or $R^2$ means a monocyclic or condensed polycyclic aromatic hydrocarbon group. Preferred examples thereof include phenyl, naphthyl, anthryl, phenanthryl, acenaphthylenyl and the like. In particular, phenyl, 1-naphthyl, 2-naphthyl and the like are preferred.

Preferred examples of the aromatic heterocyclic group as the substituent of the hydrocarbon group or heterocyclic group represented by $R^1$ or $R^2$ include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like: aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo-[1,2-a]pyridyl, imidazo[1,5-a]pyridyl, imidazo[1,2-b]-pyridazinyl, imidazo[1,2-a]pyrimidinyl, 1,2,4-triazolo[4,3-a]pyridyl, 1,2,4-triazolo[4,3-b]pyridazinyl and the like.

Preferred examples of the non-aromatic heterocyclic group as the substituent of the hydrocarbon group or heterocyclic group represented by $R^1$ or $R^2$ include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like.

The halogen atom as the substituent of the hydrocarbon group or heterocyclic group represented by $R^1$ or $R^2$ includes, for example, fluorine, chlorine, bromine and iodine. In particular, fluorine and chlorine are preferred.

The optionally substituted amino group as the substituent of the hydrocarbon group or heterocyclic group represented by $R^1$ or $R^2$ includes, for example, an amino group and a substituted amino group such as an amino group substituted by one or two substituents such as alkyl groups having 1 to 10 carbon atoms, alkenyl groups having 2 to 10 carbon atoms, aromatic groups, heterocyclic groups or acyl groups having 1 to 10 carbon atoms. These substituents of the amino group may be selected from the alkyl groups, alkenyl groups, aromatic groups, heterocyclic groups and acyl groups which are described above as the substituents of the hydrocarbon group or heterocyclic group represented by $R^1$ or $R^2$. Specific examples of the substituted amino group include methylamino, dimethylamino, ethylamino, diethylamino, dibutylamino, diallylamino, cyclohexylamino, phenylamino, N-methyl-N-phenylamino, acetylamino, propionylamino, benzoylamino, nicotinoylamino, etc.

The acyl group as the substituent of hydrocarbon group or heterocyclic group represented by $R^1$ or $R^2$ includes, for example, formyl, and ($C_{1-10}$ alkyl)-carbonyl, ($C_{2-10}$ alkenyl)-carbonyl and (aromatic cycle)-carbonyl (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, etc.).

The optionally substituted hydroxyl group as the substituent of the hydrocarbon group or heterocyclic group represented by $R^1$ or $R^2$ includes, for example, a hydroxyl group and a hydroxyl group having an appropriate substituent such as a protective group for a hydroxyl group. Examples of the hydroxyl group having such a substituent include alkoxy, alkenyloxy, aralkyloxy, acyloxy, aryloxy and the like.

Preferred examples of the alkoxy include that having 1 to 10 carbon atoms such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy, cyclohexyloxy and the like.

Examples of the alkenyloxy include that having 2 to 10 carbon atoms such as allyloxy, crotyloxy, 2-pentenyloxy, 3-hexenyloxy, 2-cyclopentenylmethoxy, 2-cyclohexenylmethoxy and the like.

Examples of the aralkyloxy include phenyl-$C_{1-4}$ alkyloxy (e.g., benzyloxy, phenethyloxy, etc.).

Preferred examples of the acyloxy include alkanoyloxy having 2 to 4 carbon atoms such as acetyloxy, propionyloxy, butyryloxy, isobutyryloxy and the like.

Examples of the aryloxy include phenoxy, 4-chlorophenoxy and the like.

The optionally substituted thiol group as the substituent of the hydrocarbon group or heterocyclic group represented by $R^1$ or $R^2$ includes, for example, a thiol group and a thiol group having an appropriate substiuent such as a protecting group for a thiol group. Examples of the thiol group having such a substituent include alkylthio, aralkylthio, acylthio and the like.

Preferred examples of the alkylthio include alkylthio having 1 to 10 carbon atoms such as methylthio, ethylthio, propylthio, isopropylthio, butylthio, isobutyltho, sec-butylthio, tert-butylthio, pentylthio, isopentylthio, neopentylthio, hexylthio, heptylthio, nonylthio, cyclobutylthio, cyclopentylthio, cyclohexylthio and the like.

Examples of the aralkylthio include phenyl-$C_{1-4}$ alkylthio (e.g., benzylthio, phenetylthio, etc.).

Preferred examples of the acylthio include alkanoylthio having 2 to 4 carbon atoms such as acetylthio, propionylthio, n-butyrylthio, isobutyrylthio and the like.

The optionally esterified carboxyl group as the substituent of the hydrocarbon group or heterocyclic group represented by $R^1$ or $R^2$ include, for example, a carboxyl group, alkyloxycarbonyl, aralkyloxycarbonyl and the like.

The alkyl group of the alkyloxycarbonyl includes alkyl groups having 1 to 6 carbon atoms such as methyl, ethyl, propyl, isopropyl, butyl, isobutyl, sec-butyl, tert-butyl, etc.

The aralkyl group of the aralkyloxycarbonyl group means an aryl-alkyl group. The aryl group of the aryl-alkyl group includes phenyl, naphthyl, etc., and the aryl group may have the above substituent(s) of the hydrocarbon group represented by $R^1$ or $R^2$. Preferred examples of the alkyl group of the aryl-alkyl group include lower alkyl groups having 1 to 6 carbon atoms such as methyl, ethyl, propyl, butyl, etc. Preferred examples of the aralkyl group include benzyl, phenethyl, 3-phenylpropyl, (1-naphthyl)methyl, (2-naphthyl)methyl, etc. In particular, benzyl, phenethyl, etc., are preferred.

The substituent of the hydrocarbon group or heterocyclic group represented by $R^1$ or $R^2$ may have at least one, preferably 1 to 3, appropriate substituents. The substituents include lower ($C_{1-8}$) alkyl groups, lower ($C_{2-10}$) alkenyl groups, lower ($C_{2-8}$) alkynyl groups, $C_{3-8}$ cycloalkyl groups, $C_{6-15}$ aryl groups, aromatic heterocyclic groups, non-aromatic heterocyclic groups, aralkyl groups, an amino group, N-monosubstituted amino groups, N,N-disubstituted amino groups, an amidino group, $C_{1-10}$ acyl groups, a carbamoyl group, N-monosubstituted carbamoyl groups (e.g., methylcarbamoyl, ethylcarbamoyl, phenylcarbamoyl, etc.), N,N-disubstituted carbamoyl groups (e.g., N,N-dimetylcarbamoyl, N,N-diethylcarbamoyl, piperidinocarbonyl, morpholinocarbonyl, etc.), a sulfamoyl group, N-monosubstituted sulfamoyl groups (e.g., methylsulfamoyl, ethylsulfamoyl, phenylsulfamoyl, p-toluenesulfamoyl, etc.), N,N-disubstituted sulfamoyl groups (e.g., N,N-dimethylsulfamoyl, N-methyl-N-phenylsulfamoyl, piperidino-sulfonyl, morpholinosulfonyl, etc.), a carboxyl group, lower ($C_{1-5}$) alkoxy-carbonyl groups (e.g., methoxycarbonyl, ethoxy-carbonyl, propoxycarbonyl, isopropoxy-carbonyl, sec-butoxycarbonyl, isobutoxycarbonyl, tert-butoxycarbonyl, etc.), a hydroxy group, lower ($C_{1-8}$) alkoxy groups, lower ($C_{2-10}$) alkenyloxy groups, $C_{3-7}$ cycloalkyloxy groups, aralkyloxy, $C_{6-15}$ aryloxy, a mercapto group, lower ($C_{1-8}$) alkylthio groups, $C_{6-14}$ aryl-$C_{1-4}$ alkylthio groups, $C_{6-14}$ arylthio groups, a sulfo group, a cyano group, an azido group, a nitro group, a nitroso group, a halogen atom, etc. These groups include the above substituents of the hydrocarbon group or heterocyclic group represented by $R^1$ or $R^2$.

Preferred examples of the optionally substituted amino group represented by R in the above formulas (I') and (I) include N,N-diethylamino and N-tert-butyl-N-ethylamino.

The heterocyclic group of the optionally substituted heterocyclic group represented by R in the above formulas (I') and (I) includes 5- to 7-membered heterocyclic groups containing one sulfur atom, nitrogen atom or oxygen atom; 5- to 6-membered heterocyclic groups containing 2 to 4 nitrogen atoms; 5- to 6-membered heterocyclic groups containing 1 to 2 nitrogen atoms, and one sulfur atom or oxygen atom. Specific examples of the heterocyclic groups include the above heterocyclic groups represented by $R^1$ or $R^2$. Each of these heterocyclic groups may form a condensed ring with a 6-membered ring containing up to 2 nitrogen atoms, benzene ring or 5-membered ring containing one sulfur atom.

Each of these heterocyclic groups may have 1 to 3 substituents at any possible position in the ring. Examples of the substituents include aliphatic chain hydrocarbon groups, alicyclic hydrocarbon groups, aryl groups, aromatic heterocyclic groups, non-aromatic heterocyclic groups, a halogen atom, a nitro group, an optionally substituted amino group, an optionally substituted acyl group, an optionally substituted hydroxy group, an optionally substituted thiol group, an optionally esterified carboxyl group, etc. Specific examples of these groups include the above substituents of the hydrocarbon group or heterocyclic group represented by $R^1$ or $R^2$.

The substituent of the heterocyclic group may further have at least one, preferably 1 to 3, appropriate substituents. The substituents include the above-mentioned lower ($C_{1-8}$) alkyl groups, lower ($C_{2-10}$) alkenyl groups, lower ($C_{2-8}$) alkynyl groups, $C_{3-8}$ cycloalkyl groups, $C_{6-15}$ aryl groups, aromatic heterocyclic groups, non-aromatic heterocyclic groups, aralkyl groups, an amino group, N-monosubstituted amino groups, N,N-disubstituted amino groups, an amidino group, $C_{1-10}$ acyl groups, a carbamoyl group, N-monosubstituted carbamoyl groups, N,N-disubstituted carbamoyl groups, a sulfamoyl group, N-monosubstituted sulfamoyl groups, N,N-disubstituted sulfamoyl groups, a carboxyl group, lower ($C_{1-5}$) alkoxy-carbonyl groups, a hydroxyl group, lower ($C_{1-8}$) alkoxy groups, lower ($C_{2-10}$) alkenyloxy groups, $C_{3-7}$ cycloalkyloxy groups, aralkyloxy groups, $C_{6-15}$ aryloxy groups, a mercapto group, lower ($C_{1-8}$) alkylthio groups, $C_{6-14}$ aryl-$C_{1-4}$ alkylthio groups, $C_{6-14}$ arylthio groups, a sulfo group, a cyano group, an azido group, a nitro group, a nitroso group, a halogen atom, etc.

Preferred examples of the optionally substituted heterocyclic group represented by R include triazolyl, imidazolyl, and morpholinyl, each of which is unsubstituted or substituted by a $C_{1-6}$ alkyl, $C_{2-6}$ alkenyl or $C_{2-6}$ alkynyl group at any possible position in the ring. More preferred examples thereof include 1,2,4-triazol-1-yl, 1-methylimidazol-2-yl, 1-imidazolyl, and mopholino.

The acyl group represented by G' or G in the formula (I') or (I) is represented, for example, by the formula: —CO—$R^3$ in which $R^3$ is an alkyl group or an aryl group. Examples of the alkyl group represented by $R^3$ include alkyl groups having 1 to 5 atoms such as methyl, ethyl, isopropyl, butyl, isobutyl, sec-butyl, tert-butyl, pentyl, isopentyl, neopentyl, tert-pentyl, 1-ethylpropyl, etc. Preferred examples of the alkyl groups include methyl, butyl, isobutyl, pentyl, etc. The aryl group represented by $R^3$ means a monocyclic or condensed polycyclic aromatic hydrocarbon group having 6 to 14 carbon atoms. Preferred examples thereof include phenyl, naphthyl, anthryl, phenanthryl, etc. In particular, phenyl, 1-naphthyl, 2-naphthyl, etc., are preferred.

The alkyl group of the hydroxyalkyl group having not less than 2 carbon atoms represented by G' includes the above alkyl groups represented by $R^1$ or $R^2$. Preferably, the hydroxyalkyl group is represented by the formula: —CH(OH)—$R^3$ in which $R^3$ is as defined above. $R^3$ in this formula is preferably methyl, ethyl, etc.

When the hydroxyalkyl group having not less than 2 carbon atoms represented by G' is protected, the protected hydroxy moiety may be the above substituted hydroxyl group as the substituent of the hydrocarbon group or heterocyclic group represented by $R^1$ or $R^2$. Preferably, the protected hydroxyalkyl group is represented by the formula: —CH$_2$OCOR$^4$ or —CH(OCOR$^4$)—$R^3$ in which $R^3$ is as defined above and $R^4$ is an alkyl group, aralkyl group or aryl group each of which may optionally be substituted. The alkyl group represented by $R^4$ includes, for example, alkyl groups having 1 to 6 carbon atoms such as methyl, ethyl, propyl, isopropyl, butyl, isobutyl, sec-butyl, tert-butyl, etc. The aralkyl group represented by $R^4$ means, for example, a $C_{6-14}$ aryl-$C_{1-4}$ alkyl group. Specific examples of the alkyl group in the aralkyl group include the above alkyl groups represented by $R^4$. Specific examples of the aryl group in the aralkyl group include phenyl, naphthyl, etc. Examples of the aralkyl group include benzyl, phenethyl, 3-phenylpropyl, (1-naphthyl)methyl, (2-naphthyl)methyl, etc. The aryl group represented by $R^4$ includes, for example, aryl group having 6 to 14 carbon atoms such as phenyl, naphthyl, etc.

The alkyl group of the hydroxyalkyl group represented by G includes the above alkyl groups represented by $R^1$ or $R^2$. Preferably, the hydroxyalkyl group is represented by the formula: —CH$_2$OH or —CH(OH)—$R^3$ in which $R^3$ is as defined above. $R^3$ in this formula is preferably methyl, ethyl, etc.

When the hydroxyalkyl group represented by G is protected, the protected hydroxy moiety may be the above substituted hydroxyl group as the substituent of the hydrocarbon group or heterocyclic group represented by $R^1$ or $R^2$. Preferably, the protected hydroxyalkyl group is represented by the formula: —CH$_2$OCOR$^4$ or —CH(OCOR$^4$)—$R^3$ in which $R^3$ is as defined above and $R^4$ is an alkyl group, aralkyl group or aryl group each of which may optionally be substituted. The alkyl group represented by $R^4$ includes, for example, alkyl groups having 1 to 6 carbon atoms such as methyl, ethyl, propyl, isopropyl, butyl, isobutyl, sec-butyl, tert-butyl, etc. The aralkyl group represented by $R^4$ means, for example, a $C_{6-14}$ aryl-$C_{1-4}$ alkyl group. Specific examples of the alkyl group in the aralkyl group include the above alkyl groups represented by $R^4$. Specific examples of the aryl group in the aralkyl group include phenyl, naphthyl, etc. Examples of the aralkyl group include benzyl, phenethyl, 3-phenylpropyl, (1-naphthyl)methyl, (2-naphthyl)methyl, etc. The aryl group represented by $R^4$ includes, for example, aryl group having 6 to 14 carbon atoms such as phenyl, naphthyl, etc.

The amidated carboxyl group represented by G is represented, for example, by the formula: —CON($R^1$)($R^2$) in which $R^1$ and $R^2$ are as defined above.

The halogen atom represented by G or G' is, for example, chlorine, bromine, iodine, or fluorine, preferably chlorine or bromine.

Each of the ring A and ring B in the formula (I) may be substituted with at least one substituent. Examples of the substituent include halogen atoms, a nitro group, optionally substituted alkyl groups, an optionally substituted hydroxyl group, an optionally substituted thiol group, an optionally substituted amino group, optionally substituted acyl groups, an optionally esterified carboxyl group, and optionally substituted aromatic cyclic groups.

The halogen atom as the substituent of the ring A and ring B includes, for example, fluorine, chlorine, bromine and iodine. In particular, fluorine and chlorine are preferred.

The optionally substituted alkyl group as the substituent of the ring A and ring B is selected from straight-chain, branched or cyclic alkyl groups having 1 to 10 carbon atoms. Specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl, cycloheptyl, etc. When the alkyl group is substituted, the substituent includes the above substituents of the hydrocarbon group or heterocyclic group represented by $R^1$ or $R^2$.

The optionally substituted hydroxyl group as the substituent of the ring A and ring B includes, for example, a hydroxyl group, and a hydroxyl group having an appropriate substituent such as a protective group for a hydroxyl group. Examples of the protected hydroxyl group include alkoxy groups, alkenyloxy groups, aralkyloxy groups, acyloxy groups, aryloxy groups, etc.

Preferred examples of the alkoxy groups include those having 1 to 10 carbon atoms such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy, etc.

Examples of the alkenyloxy groups include those having 2 to 10 carbon atoms such as allyloxy, crotyloxy, 2-pentenyloxy, 3-hexenyloxy, 2-cyclopentenylmethoxy, 2-cyclohexenylmethoxy, etc.

Examples of the aralkyloxy groups include phenyl-$C_{1-14}$ alkyloxy (e.g., benzyloxy, phenethyloxy, etc.).

Preferred examples of the acyloxy groups include alkanoyloxy groups having 2 to 4 carbon atoms such as acetyloxy, propionyloxy, butyryloxy, isobutyryloxy, etc.

Examples of the aryloxy include $C_{6-14}$ aryloxy such as phenoxy, and 4-chlorophenoxy.

The optionally substituted thiol as the substituent of the ring A and ring B includes, for example, a thiol group and a thiol group having an appropriate substituent such as a protective group for a thiol group. Examples of the substituted thiol group include alkylthio groups, aralkylthio groups, acylthio groups, etc.

Preferred examples of the alkylthio groups include those having 1 to 10 carbon atoms such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio, etc.

Examples of the aralkylthio groups include phenyl-$C_{1-4}$ alkylthio (e.g., benzylthio, phenethylthio, etc.).

Preferred examples of the acylthio groups include alkanoylthio groups having 2 to 4 carbon atoms such as acetylthio, propionylthio, butyrylthio, isobutyrylthio, etc.

The optionally substituted amino group as the substituent of the ring A and ring B includes, for example, an amino group and an amino group substituted with one or two substituents selected from alkyl groups having 1 to 10 carbon atoms, alkenyl groups having 2 to 10 carbon atoms, aromatic groups, and acyl groups. These substituents of the amino group may be selected from the alkyl groups, alkenyl groups, aromatic groups and acyl groups which are described above as the substituents of the hydrocarbon group or heterocyclic group represented by $R^1$ or $R^2$. Specific examples of the substituted amino group include methylamino, dimethylamino, ethylamino, diethylamino, dibutylamino, diallylamino, cyclohexylamino, phenylamino, N-methyl-N-phenylamino, acetylamino, propionylamino, benzoylamino, etc.

The optionally substituted acyl group as the substituent of the ring A and ring B includes, for example, formyl, and ($C_{1-10}$ alkyl)-carbonyl, ($C_{2-10}$ alkenyl)-carbonyl and (aromatic group)-carbonyl such as acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, etc. When the acyl group is substituted, the substituent may be selected from the above substituents of the hydrocarbon group or heterocyclic group represented by $R^1$ or $R^2$.

The optionally esterified carboxyl group as the substituent of the ring A and ring B includes, for example, a carboxyl group, alkyloxycarbonyl groups, and aralkyloxy-carbonyl groups. Examples of the alkyl groups of the alkyloxycarbonyl groups include alkyl groups having 1 to 6 carbon atoms such as methyl, ethyl, propyl, isopropyl, butyl, isobutyl, sec-butyl, tert-butyl, etc. The aralkyl group of the aralkyloxycarbonyl group means an arylalkyl group. Examples of the aryl group of the arylalkyl group include phenyl, naphthyl, etc. The aryl group may have the same substituent as that of the above aryl group represented by R. The alkyl group is preferably a lower alkyl group having 1 to 6 carbon atoms. Preferred examples of the aralkyl group include benzyl, phenethyl, 3-phenylpropyl, (1-naphthyl)-methyl, (2-naphthyl)methyl, etc. In particular, benzyl, phenethyl, etc., are preferred.

The optionally substituted aromatic cyclic group as the substituent of the ring A and ring B includes, for example, $C_{6-14}$ aromatic hydrocarbon groups (e.g., phenyl, naphthyl, anthryl, etc.) and aromatic heterocyclic groups (e.g., pyridyl, furyl, thienyl, imidazolyl, thiazolyl, etc.). When the aromatic cyclic group is substituted, the substituent is selected from the substituents of the hydrocarbon group or heterocyclic group represented by $R^1$ or $R^2$.

The substituent of the ring A and ring B may be at any possible position in the rings. Preferably, the ring A is substituted at the 6 and/or 7 position(s) of the quinoline ring. Preferably, the ring B is substituted at the 3 and/or 4 position(s) of the ring B. Each of the rings may be substituted with the same or different 1 to 4 substituents. When the substituents of the ring A or ring B are adjacent to each other, the adjacent substituents are linked together to form a group of the formula: —$(CH_2)_m$— or —O—$(CH_2)_l$—O— (wherein m is an integer of 3 to 5 and l is an integer of 1 to 3) which may form a 5- to 7-membered ring with carbon atoms of the benzene ring.

Preferably, the ring A is substituted with methylenedioxy at the 6- and 7-positions of the quinoline ring; the same or different alkoxy groups, in particular methoxy; or the same or different two alkoxy groups, in particular two methoxy groups at the 6- and 7-positions of the quinoline ring.

Preferably, the ring B is substituted with methylenedioxy; at least one alkoxy group, in particular methoxy; the same or different two alkoxy groups, in particular two methoxy groups; methoxy groups at the 3- or 4-position; or two methoxy groups at the 3- and 4-positions.

The optionally oxidized sulfur atom represented by X includes, for example, a sulfur atom, a sulfinyl group, and a sulfonyl group.

X is preferably —$(CH_2)_q$—. q is preferably 0 or 1.

k is preferably 0.

Preferred examples of the compound of the formula (I) or a salt thereof include:

3-acetyl-2-(N,N-diethylaminomethyl)-4-(3,4-dimethoxyphenyl)-6,7-dimethoxyquinoline, 3-acetyl-2-(N-tert-butyl-N-ethylaminomethyl)-4-(3,4-dimethoxyphenyl)-6,7-dimethoxyquinoline, 4-(3,4-dimethoxyphenyl)-6,7-dimethoxy-2-[(1-methyl-imidazol-2-yl)thiomethyl]-3-valerylquinoline, 4-(3,4-dimethoxyphenyl)-3-hexanoyl-6,7-dimethoxy-2-(1,2,4-triazol-1-ylmethyl)quinoline, and 3-chloro-2-(N,N-diethylaminomethyl)-4-(3,4-dimethoxyphenyl)-6,7-dimethoxyquinoline, or salts thereof.

The salt of the compound of the formula (I) used in the present invention is preferably a pharmaceutically acceptable salt. Examples thereof include salts with inorganic bases, organic bases, inorganic acids, organic acids, basic or acidic amino acids and the like.

Preferred examples of the salts with inorganic bases include alkaline metal salts such as a sodium salt, potassium salt, etc.; alkaline earth metal salts such as a calcium salt, magnesium salt, etc.; an aluminium salt, etc.; an ammonium salt, etc.

Preferred examples of the salts with organic bases include salts with trimethylamine, triethylamine, pyridine, picoline, ethanolamine, diethanolamine, triethanolamine, dicyclohexylamine, N,N'-dibenzylethylenediamine, etc.

Preferred examples of the salts with inorganic acids include salts with hydrochloric acid, hydrobromic acid, nitric acid, sulfuric acid, phosphoric acid, etc.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of the salts with basic amino acids include salts with arginine, lysine, ornithine, etc.

Preferred examples of the salts with acidic amino acids include aspartic acid, glutamic acid, etc.

The compound (I) (i.e., the compound of the formula (I); the compounds of other formulas are hereinafter sometimes abbreviated likewise) can be prepared, for example, as follows.

Method A

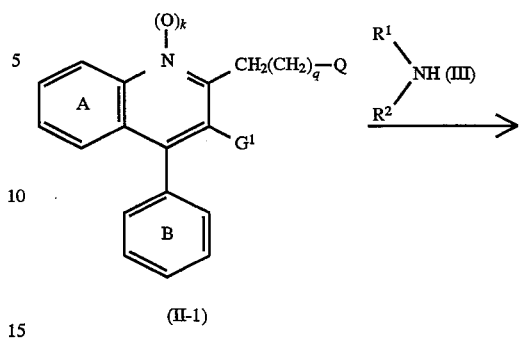

(II-1)

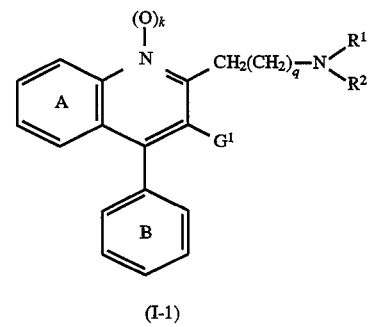

(I-1)

wherein Q is a leaving group, $G^1$ is a halogen atom or an acyl group, and the other symbols are as defined above.

The leaving group represented by Q in the formula (II-1) includes, for example, halogen (preferably chlorine, bromine, iodine), a hydroxyl group activated by esterification such as an organic sulfonic acid residue (e.g., p-toluenesulfonyloxy, methanesulfonyloxy, etc.) and an organic phosphoric acid residue (e.g., diphenylphosphoryloxy, dibenzylphosphoryloxy, dimethylphosphoryloxy, etc.).

The halogen atom and acyl group represented by $G^1$ are as defined for the halogen atom and acyl group represented by G, respectively.

In this method, the compound (II-1) is reacted with the compound (III) in the presence of a base to prepare the compound (I-1). This reaction is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethyl sulfoxide, chloroform, dichloromethane, 1,2-dichloroethane, 1,1,2,2-tetrachloroethane, acetone and 2-butanone, and mixed solvents thereof.

This reaction is carried out in the presence of an appropriate base such as an alkaline metal salt (e.g., sodium hydroxide, potassium hydroxide, sodium carbonate, potassium carbonate, sodium bicarbonate, etc.), amine (e.g., pyridine, triethylamine, N,N-dimethylaniline, etc.), sodium hydride, potassium hydride, etc. The amount of the base to be used is preferably 1 to 5 mol per mol of the compound (II-1). This reaction may be carried out using an excess amount of the compound (III) as a base.

The reaction temperature is normally −20° to 150° C., preferably about −10° to 100° C. The reaction time is normally 0.5 hour to 100 hours, preferably 1 hour to 50 hours.

The compound (I-1) thus obtained can be isolated and purified by conventional separation and purification techniques such as concentration, concentration under reduced pressure, solvent extraction, crystallization, recrystallization, redistribution, chromatography, etc.

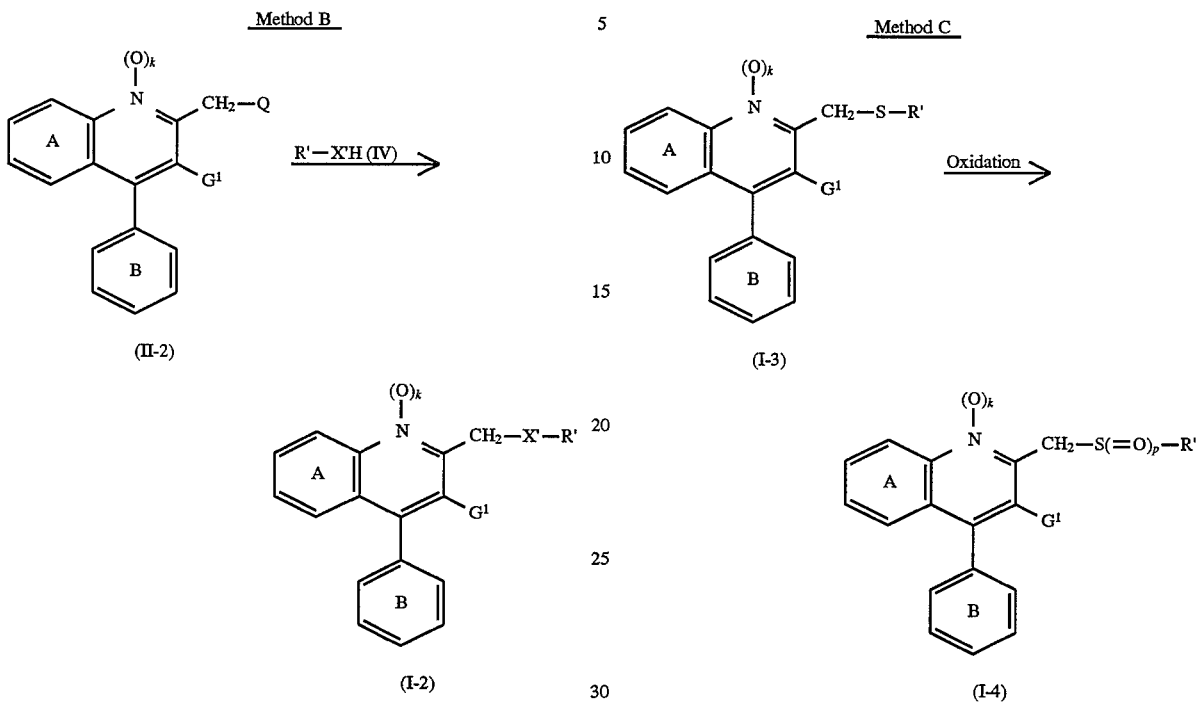

wherein R' is an optionally substituted heterocyclic group, X' is an oxygen atom or sulfur atom, and the other symbols are as defined above.

The optionally substituted heterocyclic group represented by R' in the compounds (I-2) and (IV) includes the optionally substituted heterocyclic groups represented by R.

In this method, the compound (II-2) is reacted with the compound (IV) in the presence of a base to prepare the compound (I-2). This reaction is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and mixed solvents thereof.

This reaction is carried out in the presence of an appropriate base such as an alkaline metal salt (e.g., sodium hydroxide, potassium hydroxide, sodium carbonate, sodium bicarbonate, etc.), silver carbonate ($Ag_2CO_3$), amines (e.g., pyridine, triethylamine, N,N-dimethylaniline, etc.), sodium hydride, potassium hydride, etc. The amount of the base to be used is preferably about 1 to 5 mol per mol of the compound (II-2). The reaction temperature is normally −20° to 150° C., preferably about −10° to 100° C. The reaction time is 0.5 hour to 100 hours, preferably 1 hour to 50 hours.

The compound (I-2) thus obtained can be isolated and purified by conventional separation and purification techniques such as concentration, concentration under reduced pressure, solvent extraction, crystallization, recrystallization, redistribution, chromatography, etc.

wherein p is 1 or 2, and the other symbols are as defined above.

In this method, the compound (I-2) wherein X' is a sulfur atom, i.e. the compound (I-3), prepared by Method B is subjected to oxidation to give the compound (I-4). This oxidation is carried out according to a conventional method using an oxidizing agent such as m-chloroperbenzoic acid, hydrogen peroxide, peresters, sodium metaperiodate, etc. This oxidation is preferably carried out in an organic solvent that is inert in the reaction conditions, such as halogenated hydrocarbons (e.g., methylene chloride, chloroform, dichloroethane, etc.), hydrocarbons (e.g., benzene, toluene, etc.), and alcohols (e.g., methanol, ethanol, propanol, etc.). When the oxidizing agent is used in an equimolecular amount or less based on the compound (I-3), the compound (I-4) wherein p is 1 is preferentially produced. When the oxidizing agent is used in more than an equimolecular amount, the compound (I-4) wherein p is 1 is further oxidized to give the compound (I-4) wherein p is 2. The reaction temperature is −10° to 150° C., preferably about 0° to 80° C. The reaction time is normally 0.5 to 10 hours.

The compound (I-4) thus obtained can be isolated and purified by conventional separation and purification techniques such as concentration, concentration under reduced pressure, solvent extraction, crystallization, recrystallization, redistribution, chromatography, etc.

Method D

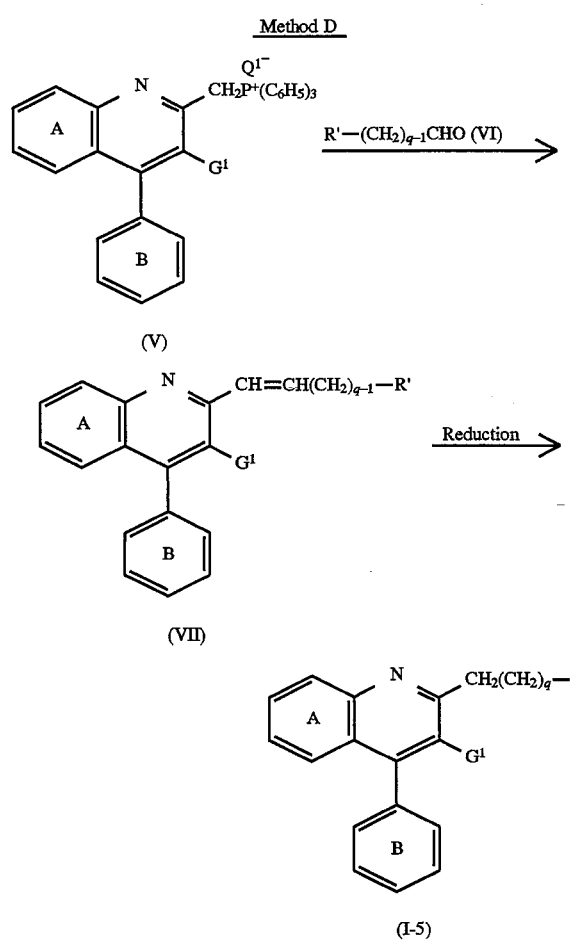

wherein Q' is a chlorine or bromine atom, and the other symbols are as defined above.

In this method, firstly, the phosphonium salt of the formula (V) and the aldehyde derivative (VI) are subjected to condensation reaction to give the compound (VII). The condensation reaction of the compound (V) with the compound (VI) is carried out in an appropriate solvent in the presence of a base.

Examples of the solvent include alcohols (e.g., methanol, ethanol, propanol, etc.), ethers (e.g., ethyl ether, dioxane, tetrahydrofuran, dimethoxyethane, etc.), aromatic hydrocarbons (e.g., benzene, toluene, xylene, etc.), dichloromethane, 1,2-dichloroethane, N,N-dimethylformamide, dimethylsulfoxide, and mixed solvents thereof.

Examples of the base include alkaline metal hydrides (e.g., sodium hydride, potassium hydride, etc.), alkoxides (e.g., sodium ethoxide, sodium methoxide, potassium ethoxide, potassium tert-butoxide, etc.), organic lithium compounds (e.g., methyllithium, butyllithium, phenyllithium, etc.), sodium amide, etc. The amount of the base to be used is about 1 to 1.5 mol per mol of the compound (V).

The reaction temperature is normally −50° to 100° C., preferably −20° to 50° C. The reaction time is 0.5 to 20 hours.

The compound (VII) is obtained as a mixture of (E)- and (Z)-isomers with respect to the newly formed double bond. After isolation of the (E)- and (Z)-isomers or without isolation, each isomer or the mixture is subjected to catalytic hydrogenation to give the compound (I-5). The catalytic hydrogenation is carried out according to a conventional method in an atmosphere of hydrogen in a solvent in the presence of a catalyst such as a palladium catalyst (e.g., palladium carbon, palladium black, etc.), platinum catalyst (e.g., platinum dioxide, etc.), Raney nickel, etc.

Examples of the solvent include alcohols (e.g., methanol, ethanol, propanol, etc.), ethers (e.g., ethyl ether, dioxane, tetrahydrofuran, dimethoxyethane, etc.), aromatic hydrocarbons (e.g., benzene, toluene, xylene, etc.), dichloromethane, 1,2-dichloroethane, ethyl acetate, acetonitrile, acetone, 2-butanone, N,N-dimethylformamide, dimethyl sulfoxide, and mixed solvents thereof. The pressure of the hydrogen atmosphere is 1 to 150 atm, preferably 1 to 20 atm.

The compound (I-5) thus obtained can be isolated and purified by conventional separation and purification techniques such as concentration, concentration under reduced pressure, solvent extraction, crystallization, recrystallization, redistribution, chromatography, etc.

Method E

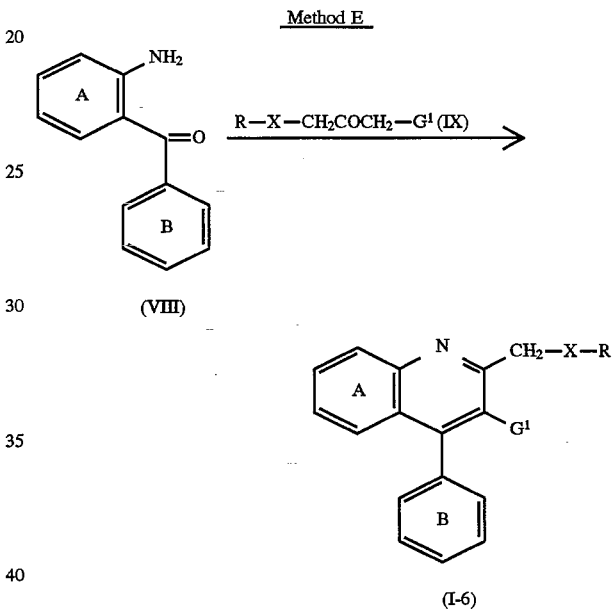

wherein each symbol is as defined above.

In this method, 2-aminobenzophenone derivative (VIII) is reacted with the compound (IX) in the presence of an acid to give the compound (I-6). This reaction is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, 2-methoxyethanol, etc.), N,N-dimethylformamide, dimethyl sulfoxide, chloroform, dichloromethane, 1,2-dichloroethane, 1,1,2,2-tetrachloroethane, acetic acid, etc.

This reaction is carried out in the presence of an appropriate acid such as Lewis acid (e.g., aluminium chloride, zinc chloride, etc.), hydrochloric acid, sulfuric acid, trifluoroacetic acid, p-toluenesulfonic acid, etc. The amount of the acid to be used is preferably 0.05 to 2.0 mol per mol of the compound (VIII). The reaction temperature is normally 20° to 200° C., preferably about 30° to 150° C. The reaction time is 0.5 to 20 hours, preferably 1 to 10 hours.

The compound (I-6) thus obtained can be isolated and purified by conventional separation and purification techniques such as concentration, concentration under reduced pressure, solvent extraction, crystallization, recrystallization, redistribution, chromatography, etc.

Method F

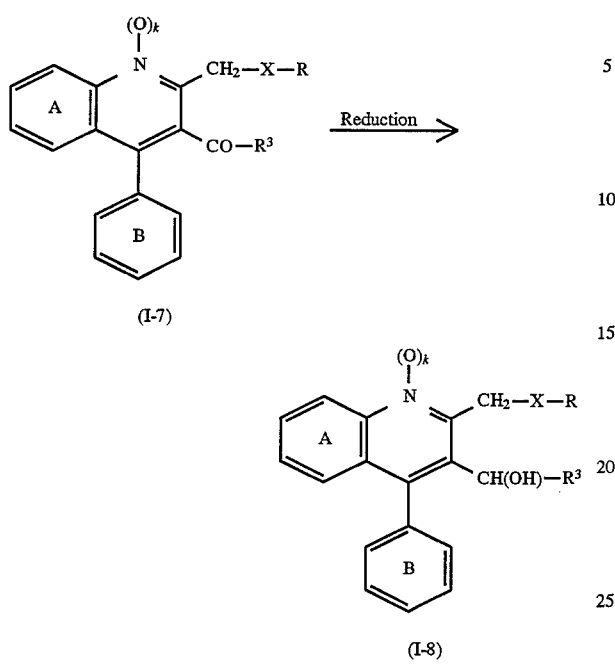

Method G

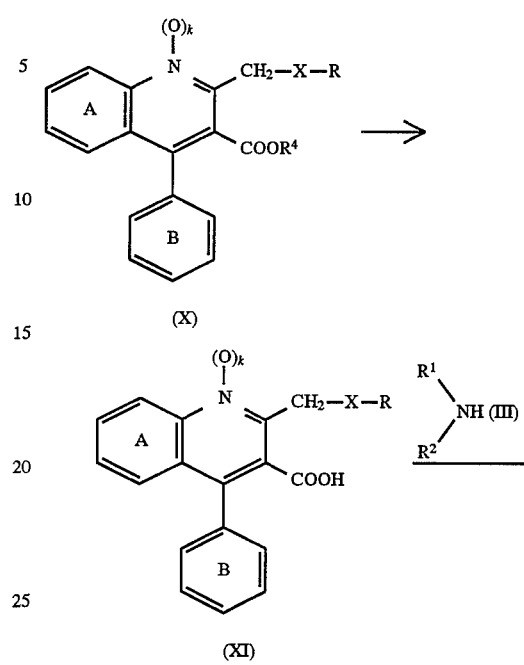

wherein each symbol is as defined above.

In this method, the compound (I-7) wherein $G^1$ is an acyl group obtained by Methods A to E is subjected to reduction to give the alcohol (I-8). This reduction can be carried out by per se known methods, for example, by reduction with a metal hydride, metal hydride complex, diborane or substituted borane, catalytic hydrogenation, etc. That is, this reaction is carried out by treating the compound (I-7) with a reducing agent. Examples of the reducing agent include metals and metal salts such as an alkaline metal borohydride (e.g., sodium borohydride, lithium borohydride, etc.), metal hydride complexes (e.g., lithium aluminum hydride, etc.), metal hydrides (e.g., sodium hydride, etc.), organic tin compounds (e.g., triphenyltin hydride, etc.), nickel compounds, zinc compounds, etc.; catalytic reducing agents, i.e., a transition metal catalyst (e.g., palladium, platinum, rhodium, etc.) and hydrogen; diborane; etc.

This reaction is carried out in an organic solvent which does not have a detrimental effect on the reaction. The solvent is appropriately selected depending upon the kind of the reducing agent. Examples of the solvent include aromatic hydrocarbons (e.g., benzene, toluene, xylene, etc.), halogenated hydrocarbons (e.g., chloroform, carbon tetrachloride, dichloromethane, 1,2-dichloroethane, 1,1,2,2-tetrachloroethane, etc.), ethers (e.g., diethyl ether, tetrahydrofuran, dioxane, etc.), alcohols (e.g., methanol, ethanol, propanol, 2-methoxyethanol, etc.), amides (e.g., N,N-dimethylformamide, etc.), mixed solvents thereof, etc. The reaction temperature is normally −20° to 150° C., preferably about 0° to 100° C. The reaction time is about 1 to 24 hours.

The compound (I-8) thus obtained can be isolated and purified by conventional separation and purification techniques such as concentration, concentration under reduced pressure, solvent extraction, crystallization, recrystallization, redistribution, chromatography, etc.

wherein each symbol is as defined above.

In this method, the ester derivative (X) is subjected to hydrolysis to give the corresponding carboxylic acid derivative (XI), which is then reacted with the compound (III) to give the amide derivative (I-9).

The compound (X) is hydrolyzed according to a conventional method in water or water-containing solvent. Examples of the water-containing solvent include alcohols (e.g., methanol, ethanol, 2-methoxyethanol, ethylene glycol, propanol, butanol, etc.), ethers (e.g., tetrahydrofuran, dioxane, etc.), acetic acid, N,N-dimethylformamide, dimethyl sulfoxide, acetonitrile, acetone, etc. This reaction is carried out in the presence of a base such as potassium carbonate, sodium carbonate, sodium hydroxide, potassium hydroxide or lithium hydroxide, or an acid such as hydrochloric acid, sulfuric acid, acetic acid or hydrobromic acid. Preferably, the acid or base is used in excess (base: 1.2 to 6 mol, acid: 2 to 50 mol per mol of the compound (X)). The reaction temperature is normally −20° to 150° C., preferably −10° to 100° C. The reaction time is 1 to 50 hours.

The condensation reaction of the compound (XI) with the compound (III) is carried out by conventional methods for peptide synthesis. The peptide synthesis method is carried out according to any per se known method, for example, the method described in Peptide Synthesis, edited by M. Bodansky and M. A. Ondetti, Interscience, New York (1966); F. M. Finn and K. Hofmann, The Proteins, Vol 2, edited by H.

Nenrath, R. L. Hill, Academic Press Inc., New York (1976); Nobuo Izumiya et al. "The basics and Experiments of Peptide Synthesis", Maruzen K. K. (1985); etc. Other methods include azide method, chloride method, acid anhydride method, mixed acid anhydride method, DCC method, activated ester method, methods using Woodward reagent K, carbonyldiimidazole method, oxidation and reduction method, DCC/HONB method, methods using diethyl phosphorocyanidate (DEPC), etc. This condensation reaction can be carried out in a solvent. Examples of the solvent include anhydrous or water-containing dimethylformamide, dimethyl sulfoxide, pyridine, chloroform, dichloromethane, tetrahydrofuran, dioxane, acetonitrile, and mixed solvent thereof. The reaction temperature is normally about −20° to about 50° C., preferably −10° to 30° C. The reaction time is 1 to 100 hours, preferably 2 to 40 hours.

The compound (I-9) thus obtained can be isolated and purified by conventional separation and purification techniques such as concentration, concentration under reduced pressure, solvent extraction, crystallization, recrystallization, redistribution, chromatography, etc.

Method H

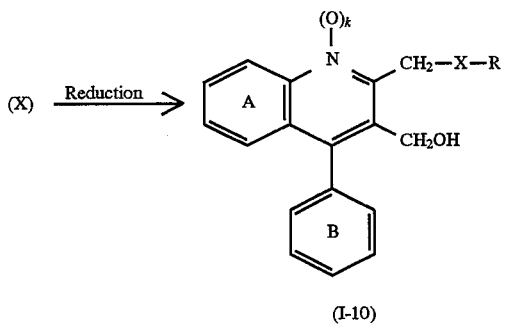

wherein each symbol is as defined above.

In this method, the compound (X) is reduced to give the alcohol (I-10). This method can be carried out according to the same manner as that described in Method F.

The compound (I-10) thus obtained can be isolated and purified by conventional separation and purification techniques such as concentration, concentration under reduced pressure, solvent extraction, crystallization, recrystallization, redistribution, chromatography, etc.

The desired salt of the compound (I) can be prepared by per se known method from the corresponding free compound or other salt.

The starting compound (X) in Methods G and H can be prepared according to EP 0567107 A1 and EP 634169 A1.

Method I

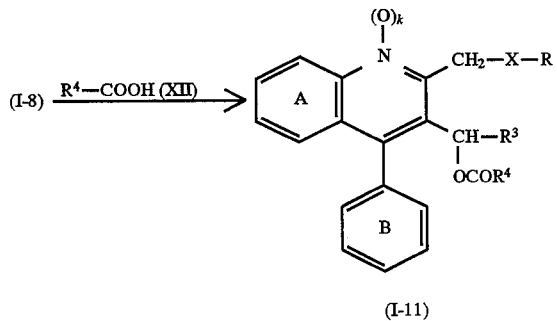

-continued
Method I

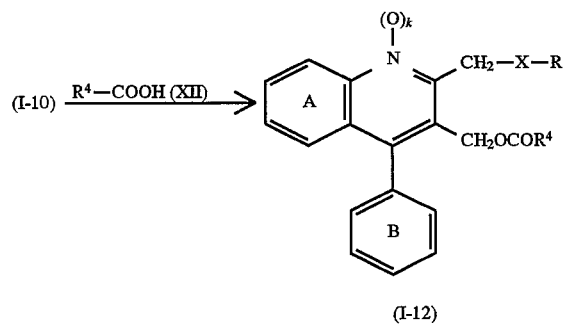

wherein each symbol is as defined above.

In this method, the alcohol derivatives (I-8) and (I-10) are acylated to give the compound (I-11) and (I-12), respectively.

In this method, the compounds (I-8) and (I-10) are reacted with the compound (XII) or a reactive derivative at the carboxyl group thereof to give the compounds (I-11) and (I-12), respectively.

The reactive derivative at the carboxyl group of the compound (XII) includes acid halides, acid anhydrides, activated amides, activated esters, etc. Preferred examples of the reactive derivative include acid chlorides; acid azides; mixed acid anhydrides with acids such as substituted phosphoric acids (e.g., dialkylphosphoric acids, phenylphosphoric acid, diphenylphosphoric acid, dibenzylphosphoric acid, halogenated phosphoric acid, etc), dialkylphosphorous acid, sulfurous acid, thiosulfuric acid, sulfuric acid, sulfonic acids (e.g., methansulfonic acid, etc.), aliphatic carboxylic acids (e.g., acetic acid, propionic acid, butyric acid, isobutyric acid, pivalic acid, pentanoic acid, isopentanoic acid, trichloroacetic acid, etc.), or aromatic carboxylic acids (e.g., benzoic acid, etc.); symmetrical acid anhydrides; activated amides with imidazole, 4-substituted imidazole, dimethylpyrazole, triazole or tetrazole; activated esters (e.g., cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxymethyl thioester, pyranyl ester, pyridyl ester, piperidyl ester, 8-quinolyl thioester, etc.); esters with N-hydroxy compounds (e.g., N,N-dimethylhydroxyamine, 1-hydroxy-2-(1H)-pyridone, N-hydroxysuccinimide, N-hydroxyphthalimide, 1-hydroxy-1H-benzotriazole, etc.). These reactive derivatives can appropriately be selected.

Normally, the reaction is carried out in a conventional solvent such as water, alcohols (e.g., methanol, ethanol, etc.), acetone, dioxane, acetonitrile, chloroform, methylene chloride, ethylene chloride, tetrahydrofuran, ethyl acetate, N,N-dimethylformamide, pyridine, etc. Any other organic solvents can be used as long as they do not have a detrimental effect on the reaction. These conventional solvents can be used as mixtures of them with water. When the compound (XII) is used as its free acid or salt in this reaction, the reaction is preferably carried out in the presence of a conventional condensing agent such as the so-called Viismeier reagent prepared by reaction with N,N'-dicyclohexylcarbodiimide, N-cyclohexyl-N'-morpholinoethyl-carbodiimide, N-cyclohexyl-N'-(4-diethylaminocyclohexyl)-carbodiimide, N,N'-diethylcarbodiimide, N,N'-diisopropyl-carbodiimide, N-ethyl-N'-(3-dimethylaminopropyl)carbodiimide, N,N'- carbonylbis(2-methylimidazole), pentamethyleneketene-N-cyclohexylimine, diphenylketene-N-cyclohexylimine, ethoxy-acetylene, 1-alkoxy-1-chloroethylene, trialkyl phosphonate, ethyl polyphosphate, isopropyl polyphosphate, phosphorous oxychloride, diphenylphosphoryl azide, thionyl chloride, oxalyl chloride, lower alkyl haloformates (e.g., ethyl chloroformate, isopropyl chloroformate, etc.), triphenylphosphine, 2-ethyl-7-hydroxybenzisoxazolium salt, 2-ethyl-5-(m-sulfophenyl) isoxazolium hydroxide intramolecular salt, N-hydroxybenzotriazole, 1-(p-chlorobenzenesulfonyloxy)-6-chloro-1H-benzotriazole, or N,N'-dimethylformamide with thionyl chloride, phosgene, trichloromethyl chloroformate, phosphorus oxychloride, etc.

The reaction may be carried out in the presence of an inorganic or organic base such as alkaline metal bicarbonates, tri(lower)alkylamines, pyridine, N-(lower)-alkylmorpholine, N,N-di(lower)alkylbenzylamine, etc. The reaction temperature is not specifically limited, but the reaction is normally carried out under cooling or warming.

The compounds (i-11) and (I-12) thus obtained can be isolated and purified by conventional separation and purification techniques such as concentration, concentration under reduced pressure, solvent extraction, crystallization, recrystallization, redistribution, chromatography, etc.

The compound (II) can be prepared, for example, as follows.

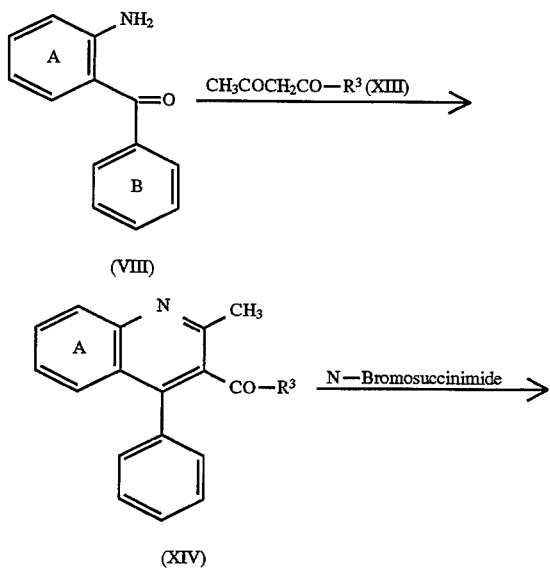

wherein each symbol is as defined above.

In this method, the 2-aminobenzophenone derivative (VIII) is reacted with the compound (XIII) in the presence of an acid to give the compound (XIV). The compound (XIV) is then brominated to give the compound (II-3). The reaction of the compound (VIII) with the compound (XIII) can be carried out according to the same manner as that of Method E.

Then, the compound (XIV) is brominated to give the 2-bromomethylquinoline derivative (II-3). The bromination of the compound (XIV) is carried out according to a conventional method, for example, by reacting it with N-bromosuccinimide, etc., in an appropriate solvent. Examples of the solvent include halogenated hydrocarbons such as carbon tetrachloride, chloroform, dichloromethane, 1,2-dichloroethane, 1,1,2,2,-tetrachloroethane, etc. The amount of N-bromosuccinimide to be used is 1 to 2 mol per mol of the compound (XIV).

The bromination is carried out in the presence of a free-radical initiator such as benzoyl peroxide, 2,2'-azobis (isobutyronitrile), etc. The amount of the free-radical initiator to be used is preferably about 0.001 to 0.01 mol per mol of the compound (XIV). The reaction temperature is normally 20° to 150° C., preferably about 30° to 100° C. The reaction time is 0.5 to 20 hours, preferably 1 to 10 hours.

The compound (II-3) thus obtained can be isolated and purified by conventional separation and purification techniques such as concentration, concentration under reduced pressure, solvent extraction, crystallization, recrystallization, redistribution, chromatography, etc.

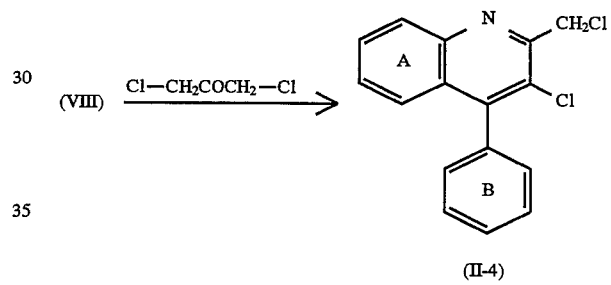

wherein each symbol is as defined above.

In this method, the 2-aminobenzophenone derivative (VIII) is reacted with 1,3-dichloroacetone to give the compound (II-4). This method is carried out according to the same manner as that described in Method E.

The compound (II-4) thus obtained can be isolated and purified by conventional separation and purification techniques such as concentration, concentration under reduced pressure, solvent extraction, crystallization, recrystallization, redistribution, chromatography, etc.

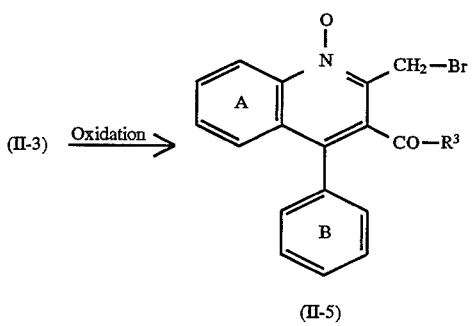

wherein each symbol is as defined above.

In this method, the compound (II-3) is oxidized to give the 1-oxide (II-5). This oxidation is carried out according to a conventional method using an oxidizing agent such as m-chloroperbenzoic acid, hydrogen peroxide, peresters, sodium metaperiodate, etc. This oxidation is preferably carried out in an organic solvent that is inert in the reaction conditions, such as halogenated hydrocarbons (e.g., methylene chloride, chloroform, dichloroethane, etc.), hydrocarbons (e.g., benzene, toluene, etc.), and alcohols (e.g., methanol, ethanol, propanol, etc.). The amount of the oxidizing agent to be used is 1 to 5 mol, preferably 1 to 3 mol, per mol of the compound (II-3). The reaction temperature is −10° to 150° C., preferably about 0° to 100° C. The reaction time is normally 0.5 to 10 hours.

The quinoline 1-oxide derivative (II-5) thus obtained can be isolated and purified by conventional separation and purification techniques such as concentration, concentration under reduced pressure, solvent extraction, crystallization, recrystallization, redistribution, chromatography, etc.

Method M

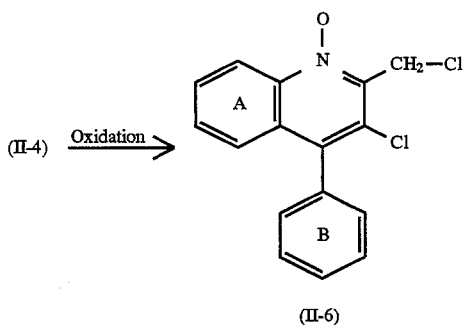

wherein each symbol is as defined above.

In this method, the compound (II-4) is oxidized to give the compound (II-6). This method is carried out according to the same manner as that described in Method L.

The quinoline derivative (II-6) thus obtained can be isolated and purified by conventional separation and purification techniques such as concentration, concentration under reduced pressure, solvent extraction, crystallization, recrystallization, redistribution, chromatography, etc.

The phosphonium salt (V) used in Method D can be prepared according to Method N.

Method N

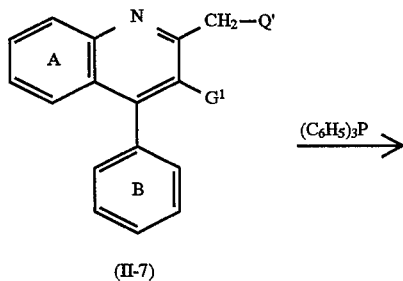

-continued
Method N

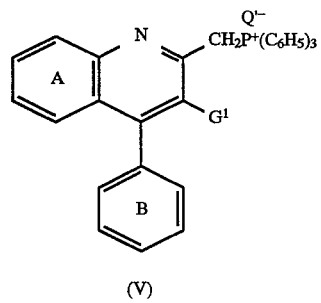

wherein each symbol is as defined above.

In this method, the compound (II-7) is reacted with an equimolecular amount of triphenylphosphine to give the phosphonium salt derivative of the formula (V). This method is carried out in a solvent. Examples of the solvent include aromatic hydrocarbons (e.g., benzene, toluene, xylene, etc.), ethers (e.g., tetrahydrofuran, dioxane, dimethoxyethane, etc.), acetonitrile, and mixed solvents thereof. The reaction temperature is 10° to 200° C., preferably 30° to 150° C. The reaction time is 0.5 to 50 hours.

The compound (I) (including the compound (I')) or a salt thereof in the present invention has anti-inflammatory activity, and antipyretic and analgesic activity. In addition, it has been confirmed that the compound (I) or a salt thereof has potent antiarthritic activity in an experimental model with adjuvant arthritis in which similar symptoms to those of human rheumatoid arthritis develop. Further, the compound (I) or a salt thereof in the present invention has low toxicity and a low risk of side effect. Thus, the compound (I) or a salt thereof of the present invention is safely applicable to the prevention and treatment of all arthritis exhibiting inflammatory symptoms in joints of mammals such as humans, mice, rats, cats, dogs, rabbits, bovines, swine, sheep and monkeys.

The compound (I) or a salt thereof of the present invention can be formulated with a pharmaceutically acceptable carrier and administered orally or parenterally as solid preparations such as tablets, capsules, granules, powders, etc; or liquid preparations such as syrups, injections, etc.

As the pharmaceutically acceptable carrier, various organic or inorganic carrier materials conventionally used for pharmaceutical preparations can be used, and formulated as excipients, lubricants, binders, disintegrators, etc., for solid preparations; solvents, solution adjuvants, suspending agents, tonicity agents, buffering agents, soothing agents, etc., for liquid preparations. If necessary, pharmaceutical additives such as antiseptics, antioxidants, colorants, sweetening agents, etc., can be used.

Preferred examples of the excipient include lactose, sucrose, D-mannitol, starch, crystalline cellulose, light anhydrous silicic acid, etc.

Preferred examples of the lubricant include magnesium stearate, calcium stearate, talc, colloidal silica, etc.

Preferred examples of the binder include crystalline cellulose, sucrose, D-mannitol, dextrin, hydroxypropylcellulose, hydroxypropylmethylcellulose, polyvinylpyrrolidone, etc.

Preferred examples of the disintegrator include starch, carboxymethylcellulose, carboxymethyl cellulose calcium, croscarmellose sodium, carboxymethyl starch sodium, etc.

Preferred examples of the solvent include water for injection, alcohols, propylene glycol, macrogol, sesame oil, corn oil, etc.

Preferred examples of the solution adjuvant include polyethylene glycol, propylene glycol, D-mannitol, benzyl benzoate, ethanol, trisaminomethane, cholesterol, triethanolamine, sodium carbonate, sodium citrate, etc.

Preferred examples of the suspending agent include surfactants such as stearyl triethanolamine, sodium lauryl sulfate, laurylaminopropionic acid, lecithin, benzalkonium chloride, benzethonium chloride, glyceryl monostearate, etc.; hydrophilic polymers such as polyvinyl alcohol, polyvinyl pyrrolidone, carboxymethylcellulose sodium, methylcellulose, hydroxymethylcellulose, hydroxyethylcellulose, hydroxypropyl-cellulose, etc.

Preferred examples of the tonicity agent include sodium chloride, glycerin, D-mannitol, etc.

Preferred examples of the buffering agent include buffers such as phosphates, acetates, carbonates, citrates, etc.

Preferred examples of the soothing agent include benzyl alcohol, etc.

Preferred examples of the antiseptics include parahydroxybenzoic acid esters, chlorobutanol, benzyl alcohol, phenethyl alcohol, dehydroacetic acid, sorbic acid, etc.

Preferred examples of the antioxidant include sulfites, ascorbic acid, etc.

The dose of the compound (I) or a salt thereof of the present invention can appropriately be selected depending upon the administration route, condition of the patient to be treated and other factors. Normally, the dose can be selected from the regions of 5 mg to 1000 mg, preferably 10 mg to 500 mg, per an average adult (b.w. 60 kg) per day in the case of oral administration, and 1 mg to 100 mg, preferably 5 to 50 mg, per an average adult (b.w. 60 kg) per day in the case of parenteral administration. The compound in the above dose can be administered daily in one to three divided portions.

As described above, the present invention provides a novel quinoline derivative having potent anti-inflammatory activity, and antipyretic and analgesic activity as well as low toxicity. In addition, the present invention provides an anti-inflammatory pharmaceutical composition that is applicable to all arthritis exhibiting inflammatory symptoms in joints.

The following experiments, reference examples, and examples further illustrate the present invention in detail, but are not to be construed to limit the scope thereof, and many changes and modifications can be made without departing from the spirit and scope of the invention.

The following experiment illustrates the pharmacological activity of the compound (I) or its salt of the present invention.

EXPERIMENT 1

Effects on Rat Adjuvant Arthritis

Male Lewis rats (7 weeks old, Charles River Japan Inc.) were sensitized by injecting Freund's complete adjuvant (a 0.5% suspension of killed *Mycobacterium tuberculosis* in liquid paraffin)(0.05 ml) intradermally into a plantar part of a right hind leg. A test drug (3.125 mg/kg) was suspended in 0.5% methylcellulose, and orally administered once a day for 14 days. The administration was started just before the sensitization (Day 0). The left hind leg volume and the body weight were measured just before the sensitization (Day 0) and on the 14th day, and the plantar edema inhibitory rate (%) and the body weight gain rate (%) based on those of non-sensitized rat groups were calculated.

The results are indicated in each group's mean (N=6) ±S.E., and assessed by Dunnett's test. The risk rate of less than 5% was evaluated as significant. As shown in Table 1, the compound of the present invention was effective in improving systemic symptoms observed as plantar edema inhibition and body weight gains.

TABLE 1

| Compound | Edema inhibitory rate (%) | Body weight gain rate[1] (%) |
|---|---|---|
| 1 | 52** | 17** |

[1] $\dfrac{\text{(Drug administered rats)} - \text{(Sensitized control rats)}}{\text{(Normal control rats)} - \text{(Sensitized control rats)}} \times 100$

**; $p < 0.01$ vs control

REFERENCE EXAMPLE 1

Conc. sulfuric acid ( 0.185 ml ) was added to a mixture of 2-amino-4,5,3',4'-tetramethoxybenzophenone ( 10.0 g), acetylacetone (3.78 g) and acetic acid (75 ml), and the mixture was stirred at 100° C. for 2.5 hours. The reaction mixture was concentrated under reduced pressure. The residue was poured into water and made alkaline with 2N sodium hydroxide, and extracted with chloroform. The chloroform layer was washed with water and dried over magnesium sulfate, and the solvent was evaporated under reduced pressure. The residue was subjected to column chromatography on silica gel. The fractions eluted with chloroform-ethanol (20:1, v/v) gave 3-acetyl-4-(3,4-dimethoxyphenyl )-6,7-dimethoxy-2-methyl-quinoline (9.78 g, 82%). This compound was recrystallized from dichloromethane-ethanol to give colorless prisms, mp. 210°–211° C.

REFERENCE EXAMPLE 2

A mixture of 3-acetyl-4-(3,4-dimethoxyphenyl)-6,7-dimethoxy-2-methylquinoline (8.5 g), N-bromosuccinimide (5. mg) , 2,2'-azobis(isobutyronitrile) (1.46 g) and carbon tetrachloride (500 ml) was stirred under reflux for 40 minutes. The reaction mixture was cooled, and then the insoluble material was filtered off. The filtrate was washed with water and dried over magnesium sulfate, and the solvent was evaporated under reduced pressure. The residue was subjected to column chromatography on silica gel. The fractions eluted with chloroform-ethyl acetate (20:1, v/v) gave 3-acetyl-2-bromomethyl-4-(3,4-dimethoxyphenyl)-6,7-dimethoxyquinoline (6.85 g, 67%). This compound was recrystallized from ethyl acetate-hexane to give colorless prisms, mp. 181°–182° C.

REFERENCE EXAMPLE 3

A mixture of 2-amino-4,5,3',4'-tetramethoxy-benzophenone hydrochloride (2.0 g), benzoylacetone (0.917 g) and ethanol (35 ml) was stirred under reflux for 1 hour. The reaction mixture was concentrated under reduced pressure. The residue was poured into a saturated aqueous solution of sodium bicarbonate, and the mixture was extracted with chloroform. The chloroform layer was washed with water, dried over magnesium sulfate, and the solvent was evaporated under reduced pressure. The residue was subjected to column chromatography on silica gel. The fractions eluted with chloroform-ethyl acetate (10:1, v/v) gave 3-benzoyl-4-(3,4-dimethoxyphenyl)-6,7-dimethoxy-2-methylquinoline (1.75 g, 70%). This compound was recrystallized from ethanol to give colorless prisms, mp. 151°–152° C.

REFERENCE EXAMPLE 4

A mixture of 2-amino-4,5,3',4'-tetramethoxy-benzophenone (25.0 g), 1,3-dichloroacetone (11.0 g), conc.

sulfuric acid (1.2 ml) and acetic acid (200 ml) was stirred at 110° C. for 4 hours. The reaction mixture was concentrated under reduced pressure. The residue was poured into water, made alkaline with 2N NaOH, and extracted with chloroform. The chloroform layer was washed with water, dried over magnesium sulfate, and the solvent was evaporated under reduced pressure. The residue was subjected to column chromatography on silica gel. The fractions eluted with chloroform-ethyl acetate (10:1, v/v) gave 3-chloro-2-chloromethyl-4-(3,4-dimethoxyphenyl)-6,7-dimethoxyquinoline (12.0 g, 38%). This compound was recrystallized from ethyl acetate-hexane to give colorless prisms, mp. 206°–207° C.

REFERENCE EXAMPLE 5

A mixture of 3-benzoyl-4-(3,4-dimethoxyphenyl)-6,7-dimethoxy-2-methylquinoline (5.5 g), N-bromosuccinimide (2.42 g), 2,2'-azobis(isobutyronitrile)(0.815 g) and carbon tetrachloride (250 ml) was stirred under reflux for 1.5 hours. The reaction mixture was cooled, and then the insoluble material was filtered off. The filtrate was washed with water and dried over magnesium sulfate, and the solvent was evaporated under reduced pressure. The residue was subjected to column chromatography on silica gel. The fractions eluted with chloroform-ethyl acetate (10:1, v/v) gave 3-benzoyl-2-bromomethyl-4-(3,4-dimethoxyphenyl)-6,7-dimethoxyquinoline (2.73 g, 42%). This compound was recrystallized from ethyl acetate-hexane to give colorless prisms, mp. 182°–183° C.

REFERENCE EXAMPLE 6

A mixture of 2-amino-3',4',4,5-tetramethoxybenzophenone hydrochloride (25.0 g), 2,4-octanedione (10.5 g) and ethanol (500 ml) was stirred under reflux for 2 hours. The solvent was evaporated under reduced pressure. The residue was poured into saturated aqueous sodium bicarbonate solution, and extracted with chloroform. The chloroform layer was washed with water and dried over magnesium sulfate. The chloroform was evaporated, and the residue was subjected to column chromatography on silica gel. The fractions eluted with chloroform-ethanol (20:1, v/v) gave 4-(3,4-dimethoxyphenyl)-6,7-dimethoxy-2-methyl-3-valerylquinoline- This compound was recrystallized from ethanol to give colorless prisms. mp. 119°–120° C.

REFERENCE EXAMPLE 7

According to the same manner as that described in Reference Example 6, 2-amino-3',4',4,5-tetramethoxybenzophenone hydrochloride was reacted with 2,4-nonanedione to give 4-(3,4-dimethoxyphenyl)-3-hexanoyl-6,7-dimethoxy-2-methylquinoline. This compound was recrystallized from ethanol to give colorless prisms. mp. 123°–125° C.

REFERENCE EXAMPLE 8

According to the same manner as that described in Reference Example 6, 2-amino-3',4',4,5-tetramethoxybenzophenone hydrochloride was reacted with 6-methyl-2,4-heptanedione to give 4-(3,4-dimethoxyphenyl)-3-isovaleryl-6,7-dimethoxy-2-methylquinoline. This compound was recrystallized from ethyl acetate-hexane to give colorless prisms. mp. 135°–137° C.

REFERENCE EXAMPLE 9

According to the same manner as that described in Reference Example 5, 4-(3,4-dimethoxyphenyl)-6,7-dimethoxy-2-methyl-3-valerylquinoline was brominated with N-bromosuccinimide (NBS) to give 2-bromomethyl-4-(3,4-dimethoxyphenyl)-6,7-dimethoxy-3-valerylquinoline. This compound was recrystallized from ethyl acetate-hexane to give colorless prisms. mp. 150°–151° C.

REFERENCE EXAMPLE 10

According to the same manner as that described in Reference Example 5, 4-(3,4-dimethoxyphenyl)-3-hexanoyl-6,7-dimethoxy-2-methylquinoline was brominated with N-bromo-succinimide (NBS) to give 2-bromomethyl-4-(3,4-dimethoxy-phenyl)-3-hexanoyl-6,7-dimethoxyquinoline- This compound was recrystallized from ethyl acetate-hexane to give colorless prisms. mp. 146°–147° C.

REFERENCE EXAMPLE 11

According to the same manner as that described in Reference Example 5, 4-(3,4-dimethoxyphenyl)-3-isovaleryl-6,7-dimethoxy-2-methylquinoline was brominated with N-bromo-succinimide (NBS) to give 2-bromomethyl-4-(3,4-dimethoxyphenyl)-3-isovaleryl-6,7-dimethoxyquinoline. This compound was recrystallized from ethyl acetate - hexane to give colorless prisms. mp. 159°–161° C.

EXAMPLE 1

A mixture of 3-acetyl-2-bromomethyl-4-(3,4-dimethoxyphenyl)-6,7-dimethoxyquinoline (3.0 g), diethylamine (4.76 g) and dichloromethane (50 ml) was stirred under reflux for 14 hours. The reaction mixture was washed with water, dried over magnesium sulfate, and the solvent was evaporated. The residue was subjected to column chromatography on silica gel. The fractions eluted with chloroform gave 3-acetyl-2-(N,N-diethylaminomethyl)-4-(3,4-dimethoxyphenyl)-6,7-dimethoxyquinoline (2.07 g, 73%). This compound was recrystallized from ethyl acetate-hexane to give colorless prisms, mp. 146°–148° C.

EXAMPLE 2

3-Acetyl-2-(N,N-diethylaminomethyl)-4-(3,4-dimethoxyphenyl)-6,7-dimethoxyquinoline (0.5 g) was added to an ice-cooled suspension of lithium aluminum hydride (0.045 g) in tetrahydrofuran (10 ml). The mixture was stirred at room temperature for 20 minutes. Then, water (0.3 ml) was added, and the insoluble material was filtered off. The filtrate was concentrated under reduced pressure. The residue was subjected to column chromatography on silica gel. The fractions eluted with chloroform-ethanol (20:1, v/v) gave 2-(N,N-diethylaminomethyl)-4-(3,4-dimethoxyphenyl)-3-(1-hydroxyethyl)-6,7-dimethoxyquinoline (0.23 g, 45%). This compound was recrystallized from ethyl acetate-hexane to give colorless prisms, mp. 144°–145° C.

EXAMPLE 3

Oily sodium hydride (60%, 0.372 g) was added to a solution of 1H-1,2,4-triazole (0.594 g) in N,N-dimethylformamide (30 ml), and the mixture was stirred at room temperature for 15 minutes. Then, 3-acetyl-2-bromomethyl-4-(3,4-dimethoxyphenyl)-6,7-dimethoxyquinoline (3.3 g) was added, and the mixture was stirred at 80° C. for 40 minutes. The reaction mixture was poured into water, and extracted with ethyl acetate. The ethyl acetate layer was washed with water, dried over magnesium sulfate, and the solvent was evaporated. The residue was subjected to column chromatography on silica gel. The fractions eluted with chloroform gave 3-acetyl-4-(3,4-dimethoxyphenyl)-6,7-dimethoxy-2-(1,2,4-triazol-1-ylmethyl)quinoline (1.4 g, 42%). This compound was recrystallized from ethanol to give colorless prisms, mp. 180°–181° C.

EXAMPLE 4

A mixture of 3-acetyl-2-bromomethyl-4-(3,4-dimethoxyphenyl)-6,7-dimethoxyquinoline (1.5 g), 1-methyl-2-mercaptoimidazole (0.417 g), potassium carbonate (0.495 g) and N,N-dimethylformamide (20 ml) was stirred at room temperature for 3 hours. The reaction mixture was poured into water, and extracted with ethyl acetate. The ethyl acetate layer was washed with water, and dried over magnesium sulfate. Evaporation of the solvent gave 3-acetyl-4-(3,4-dimethoxy-phenyl)-6,7-dimethoxy-2-[(1-methylimidazol-2-yl)thiomethyl]-quinoline (1.1 g, 71%). This compound was recrystallized from ethanol to give colorless prisms, mp. 175°–176° C.

EXAMPLE 5

A mixture of 3-acetyl-2-bromomethyl-4-(3,4-dimethoxyphenyl)-6,7-dimethoxyquinoline (1.5 g), morpholine (1.42 g) and dichloromethane (30 ml) was stirred at room temperature for 15 hours. The reaction mixture was washed with water, dried over magnesium sulfate, and the solvent was evaporated. The residue was subjected to column chromatography on silica gel. The fractions eluted with chloroform gave 3-acetyl-4-(3,4-dimethoxyphenyl)-2-morpholino-methyl-6,7-dimethoxyquinoline (1.1 g, 72%). This compound was recrystallized from ethyl acetate-hexane to give colorless prisms, mp. 197°–199° C.

EXAMPLE 6

A mixture of 3-benzoyl-2-bromomethyl-4-(3,4-dimethoxyphenyl)-6,7-dimethoxyquinoline (1.5 g), diethylamine (1.05 g) and dichloromethane (40 ml) was stirred under reflux for 14 hours. The reaction mixture was washed with water, dried over magnesium sulfate, and the solvent was evaporated. The residue was subjected to column chromatography on silica gel. The fractions eluted with chloroform gave 3-benzoyl-2-(N,N-diethylaminomethyl)-4-(3,4-dimethoxyphenyl)-6,7-dimethoxyquinoline (0.97 g, 66%). This compound was recrystallized from ethyl acetate-hexane to give colorless prisms, mp. 150°–151° C.

EXAMPLE 7

A mixture of 3-chloro-2-chloromethyl-4-(3,4-dimethoxyphenyl)-6,7-dimethoxyquinoline (2.0 g), diethylamine (2.5 g) and dichloromethane (50 ml) was stirred under reflux for 14 hours. The reaction mixture was washed with water, dried over magnesium sulfate, and the solvent was evaporated. The residue was subjected to column chromatography on silica gel. The fractions eluted with chloroform gave 3-chloro-2-(N,N-diethylaminomethyl)-4-(3,4-dimethoxyphenyl)-6,7-dimethoxyquinoline (1.47 g, 67%). This compound was recrystallized from ethyl acetate-hexane to give colorless prisms, mp. 146°–148° C.

EXAMPLE 8

According to the same manner as that described in Example 4, 3-benzoyl-2-bromomethyl-4-(3,4-dimethoxyphenyl)-6,7-dimethoxyquinoline was reacted with 2-mercapto-1-methylimidazole to give 3-benzoyl-4-(3,4-dimethoxyphenyl)-6,7-dimethoxy-2-[(1-methylimidazol-2-yl)thiomethyl]quinoline. This compound was recrystallized from ethanol to give colorless prisms. mp. 185°–186° C.

EXAMPLE 9

According to the same manner as that described in Example 3, 3-benzoyl-2-bromomethyl-4-(3,4-dimethoxyphenyl)-6,7-dimethoxyquinoline was reacted with imidazole to give 3-benzoyl-4-(3,4-dimethoxyphenyl)-2-(1-imidazolylmethyl)-6,7-dimethoxyquinoline. This compound was recrystallized from ethanol to give colorless prisms. mp. 214°–215° C.

EXAMPLE 10

According to the same manner as that described in Example 1, 3-acetyl-2-bromomethyl-4-(3,4-dimethoxyphenyl)-6,7-dimethoxyquinoline was reacted with N-tert-butyl-N-ethylamine to give 3-acetyl-2-(N-tert-butyl-N-ethylaminomethyl)-4-(3,4-dimethoxyphenyl)-6,7-dimethoxyquinoline. This compound was recrystallized from methanol to give colorless prisms. mp. 156°–157° C.

EXAMPLE 11

According to the same manner as that described in Example 1, 2-bromomethyl-4-(3,4-dimethoxyphenyl)-6,7-dimethoxy-3-valerylquinoline was reacted with N-tert-butyl-N-ethylamine to give 4-(3,4-dimethoxyphenyl)-2-(N-tert-butyl-N-ethylaminomethyl)-6,7-dimethoxy-3-valerylquinoline. This compound was recrystallized from ethyl acetate-hexane to give colorless prisms. mp. 137°–139° C.

EXAMPLE 12

According to the same manner as that described in Example 5, 2-bromomethyl-4-(3,4-dimethoxyphenyl)-6,7-dimethoxy-3-valerylquinoline was reacted with morpholine to give 4-(3,4-dimethoxyphenyl)-6,7-dimethoxy-2-morpholinomethyl-3-valerylquinoline. This compound was recrystallized from ethyl acetate-hexane to give colorless prisms. mp. 137°–138° C.

EXAMPLE 13

According to the same manner as that described in Example 1, 2-bromomethyl-4-(3,4-dimethoxyphenyl)-6,7-dimethoxy-3-hexanoylquinoline was reacted with diethylamine to give 2-(N,N-diethylaminomethyl)-4-(3,4-dimethoxyphenyl)-3-hexanoyl-6,7-dimethoxyquinoline. This compound was recrystallized from ethyl acetate - hexane to give colorless prisms. mp. 104°–106° C.

EXAMPLE 14

According to the same manner as that described in Example 5, 2-bromomethyl-4-(3,4-dimethoxyphenyl)-3-hexanoyl-6,7-dimethoxyquinoline was reacted with morpholine to give 4-(3,4-dimethoxyphenyl)-3-hexanoyl-6,7-dimethoxy-2-morpholino-methylquinoline. This compound was recrystallized from ethyl acetate-hexane to give colorless prisms. mp. 154°–155° C.

EXAMPLE 15

According to the same manner as that described in Example 5, 2-bromomethyl-4-(3,4-dimethoxyphenyl)-3- isovaleryl-6,7-dimethoxyquinoline was reacted with morpholine to give 4-(3,4-dimethoxyphenyl)-3-isovaleryl-6,7-dimethoxy-2-morpholino-methylquinoline. This compound was recrystallized from ethyl acetate-hexane to give colorless prisms. mp. 138°–140° C.

EXAMPLE 16

According to the same manner as that described in Example 4, 2-bromomethyl-4-(3,4-dimethoxyphenyl)-6,7-dimethoxy-3-isovalerylquinoline was reacted with 2-mercapto-1-methylimidazole to give 4-(3,4-dimethoxyphenyl)-6,7-dimethoxy-2-[(1-methylimidazol-2-yl)thiomethyl]-3-valerylquinoline. This compound was recrystallized from ethyl acetate-hexane to give colorless prisms. mp. 125°–127° C.

EXAMPLE 17

According to the same manner as that described in Example 4, 2-bromomethyl-4-(3,4-dimethoxyphenyl)-3-hexanoyl-6,7-dimethoxyquinoline was reacted with 2-mercapto-1-methylimidazole to give 4-(3,4-dimethoxyphenyl)-3-hexanoyl-6,7-dimethoxy-2-[(1-methylimidazol-2-yl)thiomethyl]quinoline. This compound was recrystallized from ethanol to give colorless prisms. mp. 128°–129° C.

EXAMPLE 18

According to the same manner as that described in Example 4, 2-bromomethyl-4-(3,4-dimethoxyphenyl)-3-isovaleryl-6,7-dimethoxyquinoline was reacted with 2-mercapto-1-methylimidazole to give 4-(3,4-dimethoxyphenyl)-3-isovaleryl-6,7-dimethoxy-2-[(1-methylimidazol-2-yl)thiomethyl]quinoline. This compound was recrystallized from ethanol to give colorless prisms. mp. 152°–153° C.

EXAMPLE 19

According to the same manner as that described in Example 3, 2-bromomethyl-4-(3,4-dimethoxyphenyl)-6,7-dimethoxy-3-valerylquinoline was reacted with imidazole to give 4-(3,4-dimethoxyphenyl)-2-(1-imidazolylmethyl)-6,7-dimethoxy-3-valerylquinoline. This compound was recrystallized from ethanol to give colorless prisms. mp. 156°–157° C.

EXAMPLE 20

According to the same manner as that described in Example 3, 2-bromomethyl-4-(3,4-dimethoxyphenyl)-3-isovaleryl-6,7-dimethoxyquinoline was reacted with imidazole to give 4-(3,4-dimethoxyphenyl)-2-(1-imidazolylmethyl)-3-isovarelyl-6,7-dimethoxyquinoline. This compound was recrystallized from ethyl acetate-hexane to give colorless prisms. mp. 180°–181° C.

EXAMPLE 21

According to the same manner as that described in Example 3, 2-bromomethyl-4-(3,4-dimethoxyphenyl)-3-hexanoyl-6,7-dimethoxyquinoline was reacted with 1H-1,2,4-triazole to give 4-(3,4-dimethoxyphenyl)-3-hexanoyl-6,7-dimethoxy-2-(1,2,4-triazol-1-ylmethyl)quinoline. This compound was recrystallized from ethanol to give colorless prisms. mp. 151°–152° C.

EXAMPLE 22

According to the same manner as that described in Example 1, 2-bromomethyl-4-(3,4-dimethoxyphenyl)-3-isovaleryl-6,7-dimethoxyquinoline was reacted with diethylamine to give 2-(N,N-diethylaminomethyl)-4-(3,4-dimethoxyphenyl) -3-isovaleryl-6,7-dimethoxyquinoline. This compound was recrystallized from ethyl acetate-hexane to give colorless prisms. mp. 153°–154° C.

The chemical formulas of the compounds obtained in Reference Examples (Refo) and Examples (Ex.) above are listed in the following tables. In the tables, Et means ethyl, and tBu means tert-butyl.

| Ref. No. | |
|---|---|
| 1 | 4-(3,4-dimethoxyphenyl)-6,7-dimethoxy-2-methyl-3-acetylquinoline structure (2-CH$_3$, 3-COCH$_3$) |
| 2 | 2-CH$_2$Br, 3-COCH$_3$ analog |
| 3 | 2-CH$_3$, 3-COC$_6$H$_5$ analog |
| 4 | 2-CH$_2$Cl, 3-Cl analog |
| 5 | 2-CH$_2$Br, 3-COC$_6$H$_5$ analog |

-continued
Ref. No.
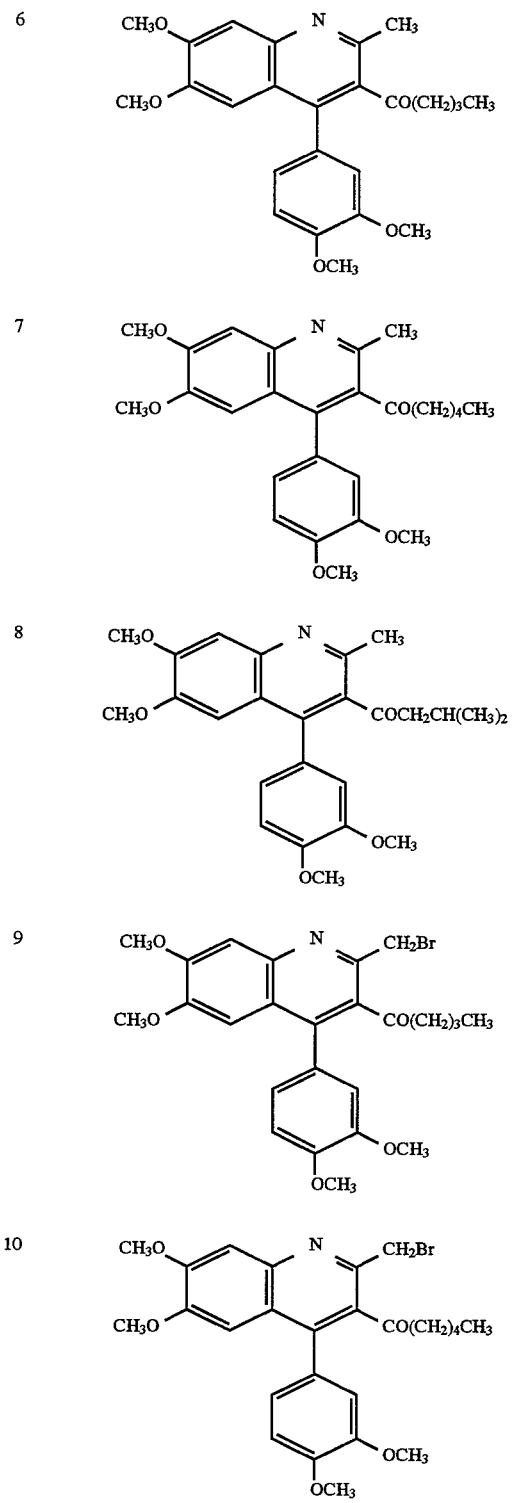
-continued
Ref. No.
11
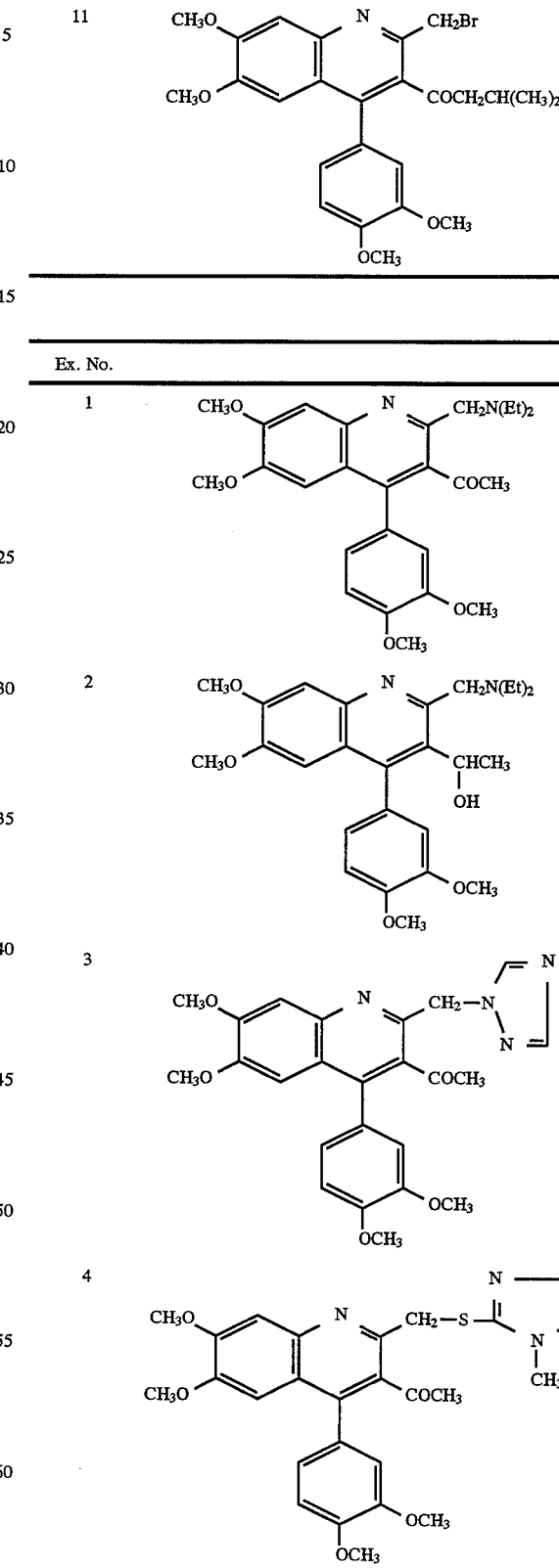
Ex. No.
1
2
3
4

| Ex. No. | | Ex. No. | |
|---|---|---|---|
| 5 | 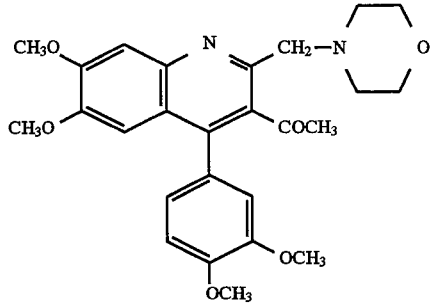 | 10 | 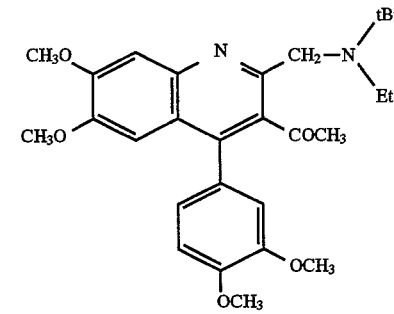 |
| 6 | 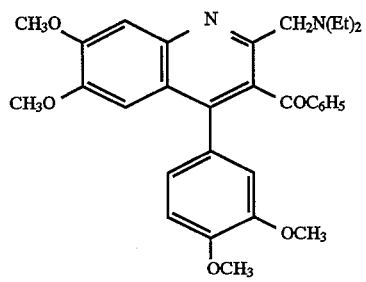 | 11 | 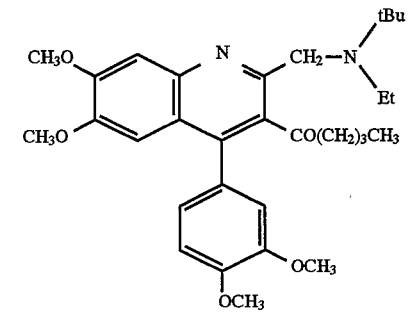 |
| 7 | 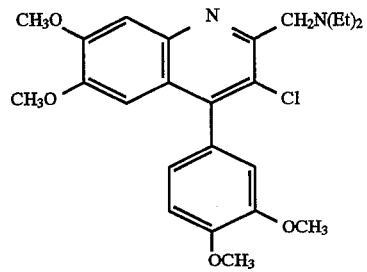 | 12 | 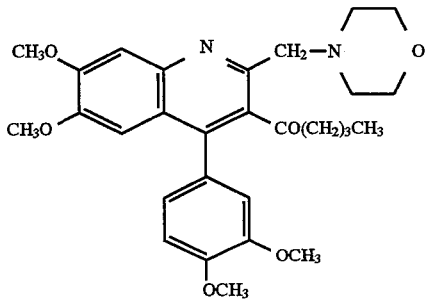 |
| 8 | 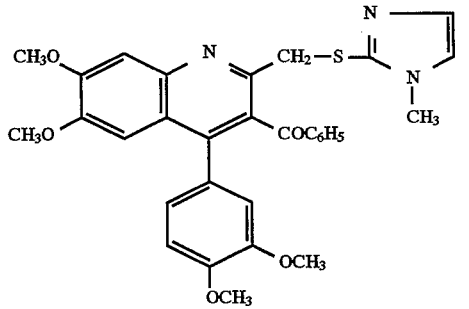 | 13 | 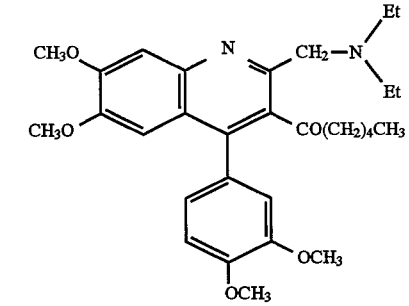 |
| 9 | 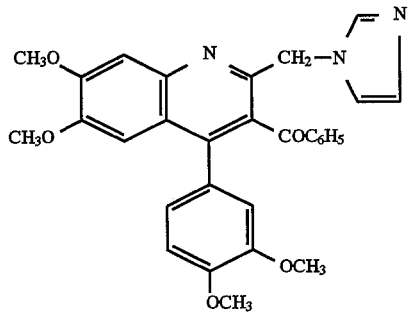 | 14 | 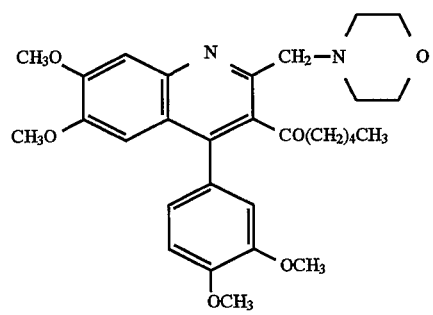 |

| Ex. No. | |
|---|---|
| 15 | 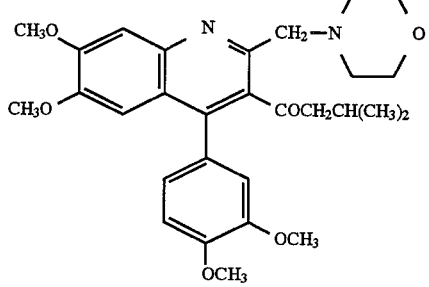 |
| 16 | 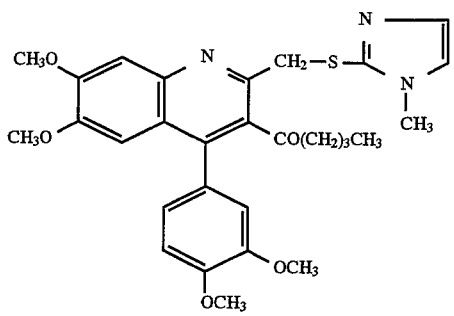 |
| 17 | 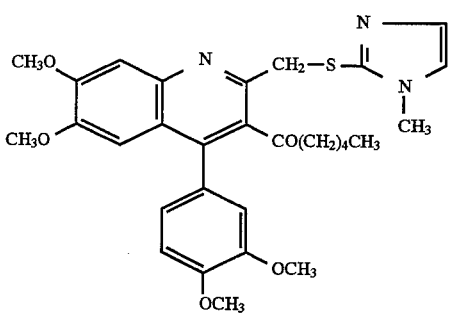 |
| 18 | 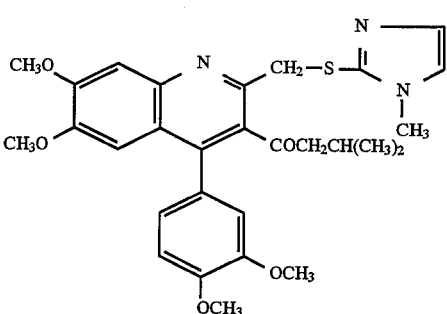 |
| 19 | 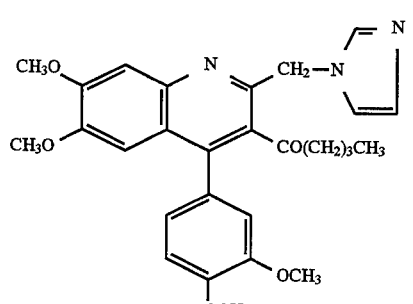 |

| Ex. No. | |
|---|---|
| 20 | 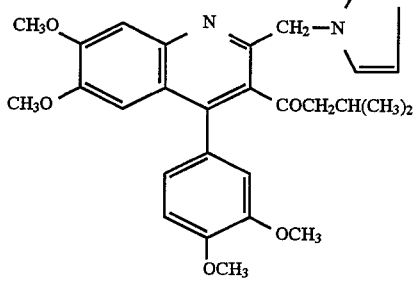 |
| 21 | 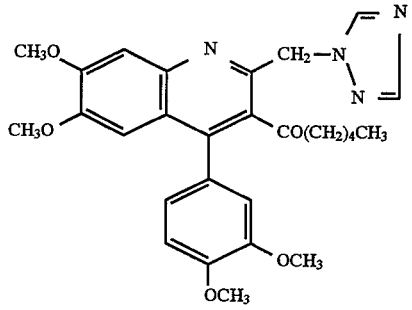 |
| 22 | 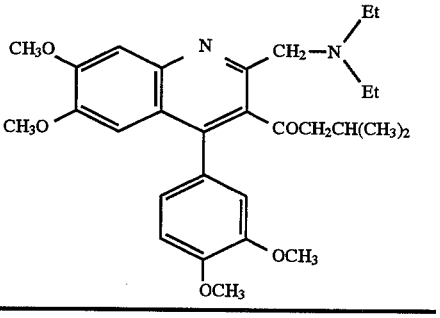 |

What is claimed is:

1. A compound of the formula (I'):

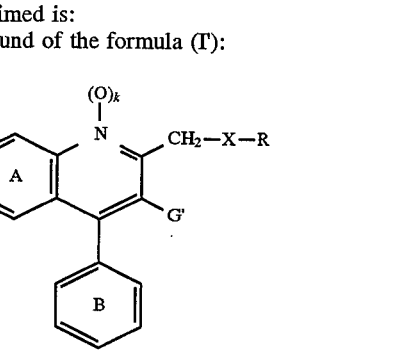

wherein

G' is an acyl group, optionally protected hydroxyalkyl group having not less than 2 carbon atoms, or halogen atom;

X is an oxygen atom, optionally oxidized sulfur atom or —$(CH_2)_q$— in which q is an integer of 0 to 5;

R is an optionally substituted amino group or optionally substituted heterocyclic group;

each of the ring A and ring B may optionally be substituted; and k is 0 or 1;

or a salt thereof.

2. The compound according to claim 1, wherein X is —(CH$_2$)$_q$— in which q is 0 or 1, or salt thereof.

3. The compound according to claim 1, wherein R is an optionally substituted amino group, or a salt thereof.

4. The compound according to claim 3, wherein the substituent of the optionally substituted amino group represented by R is an optionally substituted alkyl group, or a salt thereof.

5. The compound according to claim 1, wherein the optionally substituted heterocyclic group represented by R is an aromatic 5-membered heterocyclic group containing 2 to 3 heteroatoms, or a salt thereof.

6. The compound according to claim 1, wherein the optionally substituted heterocyclic group represented by R is a 5- to 7-membered heterocyclic group containing one sulfur atom, nitrogen atom or oxygen atom, a 5- to 6-membered heterocyclic group containing 2 to 4 nitrogen atoms or a 5- to 6-membered heterocyclic group containing 1 to 2 nitrogen atoms and one sulfur atom or oxygen atom, each of which may optionally be substituted, or a salt thereof.

7. The compound according to claim 1, wherein X is a thio group, sulfinyl group or sulfonyl group, or a salt thereof.

8. The compound according to claim 1, wherein G' is an acyl group, or a salt thereof.

9. The compound according to claim 8, wherein G' is an acetyl group, or a salt thereof.

10. The compound according to claim 1, wherein the ring A is substituted with at least one alkoxy group, or a salt thereof.

11. The compound according to claim 10, wherein the ring A is substituted with the same or different two alkoxy groups, or a salt thereof.

12. The compound according to claim 11, wherein the ring A is substituted with two alkoxy groups at the 6- and 7-positions of the quinoline ring, or a salt thereof.

13. The compound according to claim 1, wherein the ring B is substituted with at least one alkoxy group, or a salt thereof.

14. The compound according to claim 13, wherein the ring B is substituted with the same or different two alkoxy groups, or a salt thereof.

15. The compound according to claim 14, wherein the ring B is substituted with two alkoxy groups at the 3- and 4-positions, or a salt thereof.

16. The compound according to claim 1, wherein k is 0, or a salt thereof.

17. The compound according to claim 1, which is
3-acetyl-2-(N,N-diethylaminomethyl)-4-(3,4-dimethoxyphenyl)-6,7-dimethoxyquinoline, or a salt thereof.

18. A pharmaceutical composition comprising a compound represented by the formula (I):

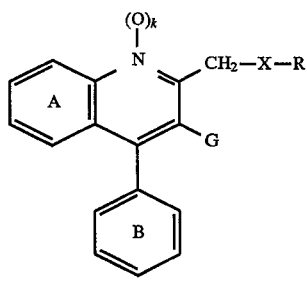

wherein
G is an acyl group, optionally protected hydroxyalkyl group, amidated carboxyl group or halogen atom;

X is an oxygen atom, optionally oxidized sulfur atom or —(CH$_2$)$_q$— in which q is an integer of 0 to 5;

R is an optionally substituted amino group or optionally substituted heterocyclic group;

each of the ring A and ring B may optionally be substituted; and k is 0 or 1;

or a pharmaceutically acceptable salt thereof, and a pharmaceutically acceptable carrier.

19. An anti-inflammatory composition comprising an effective amount of a compound represented by the formula (I):

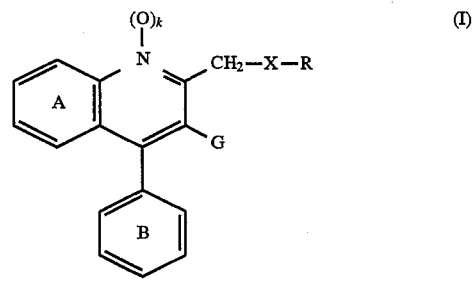

wherein

G is an acyl group, optionally protected hydroxyalkyl group, amidated carboxyl group or halogen atom;

X is an oxygen atom, optionally oxidized sulfur atom or —(CH$_2$)$_q$— in which q is an integer of 0 to 5;

R is an optionally substituted amino group or optionally substituted heterocyclic group;

each of the ring A and ring B may optionally be substituted; and k is 0 or 1;

or a pharmaceutically acceptable salt thereof, and a pharmaceutically acceptable carrier.

20. A method of preventing or treating an inflammatory disease in a mammal which comprises administering to such mammal in need thereof an effective amount of a compound of the formula (I):

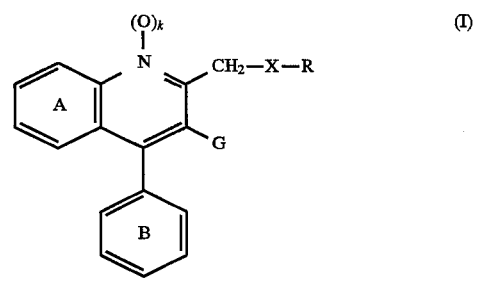

wherein

G is an acyl group, optionally protected hydroxyalkyl group, amidated carboxyl group or halogen atom;

X is an oxygen atom, optionally oxidized sulfur atom or —(CH$_2$)$_q$— in which q is an integer of 0 to 5;

R is an optionally substituted amino group or optionally substituted heterocyclic group;

each of the ring A and ring B may optionally be substituted; and k is 0 or 1;

or a pharmaceutically acceptable salt thereof, and a pharmaceutically acceptable carrier.

21. An anti-arthritic composition comprising effective amount of a compound represented by the formula (I):

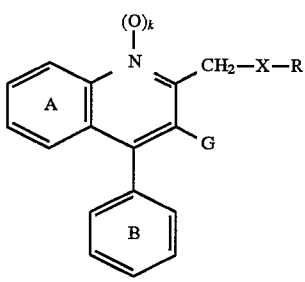

wherein
G is an acyl group, optionally protected hydroxyalkyl group, amidated carboxyl group or halogen atom;
X is an oxygen atom, optionally oxidized sulfur atom or —$(CH_2)_q$— in which q is an integer of 0 to 5;
R is an optionally substituted amino group or optionally substituted heterocyclic group;
each of the ring A and ring B may optionally be substituted; and
k is 0 or 1;
or a pharmaceutically acceptable salt thereof, and a pharmaceutically acceptable carrier.

22. An anti-rheumatic composition comprising effective amount of a compound represented by the formula (I):

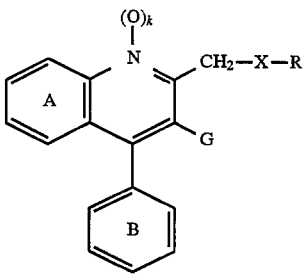

wherein
G is an acyl group, optionally protected hydroxyalkyl group, amidated carboxyl group or halogen atom;
X is an oxygen atom, optionally oxidized sulfur atom or —$(CH_2)_q$— in which q is an integer of 0 to 5;
R is an optionally substituted amino group or optionally substituted heterocyclic group;
each of the ring A and ring B may optionally be substituted; and
k is 0 or 1;
or a pharmaceutically acceptable salt thereof, and a pharmaceutically acceptable carrier.

23. An anti-pyretic analgesic composition comprising effective amount of a compound represented by the formula (I):

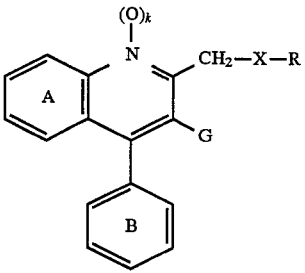

wherein
G is an acyl group, optionally protected hydroxyalkyl group, amidated carboxyl group or halogen atom;
X is an oxygen atom, optionally oxidized sulfur atom or —$(CH_2)_q$— in which q is an integer of 0 to 5;
R is an optionally substituted amino group or optionally substituted heterocyclic group;
each of the ring A and ring B may optionally be substituted; and
k is 0 or 1;
or a pharmaceutically acceptable salt thereof, and a pharmaceutically acceptable carrier.

24. A method of preventing or treating arthritis in a mammal which comprises administering to such mammal in need thereof an effective amount of a compound of the formula (I):

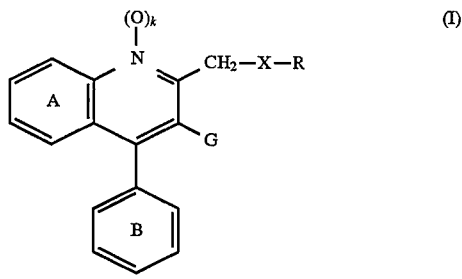

wherein
G is an acyl group, optionally protected hydroxyalkyl group, amidated carboxyl group or halogen atom;
X is an oxygen atom, optionally oxidized sulfur atom or —$(CH_2)_q$— in which q is an integer of 0 to 5;
R is an optionally substituted amino group or optionally substituted heterocyclic group;
each of the ring A and ring B may optionally be substituted; and
k is 0 or 1;
or a pharmaceutically acceptable salt thereof, and a pharmaceutically acceptable carrier.

25. A method of preventing or treating rheumatoid arthritis in a mammal which comprises administering to such mammal in need thereof an effective amount of a compound of the formula (I):

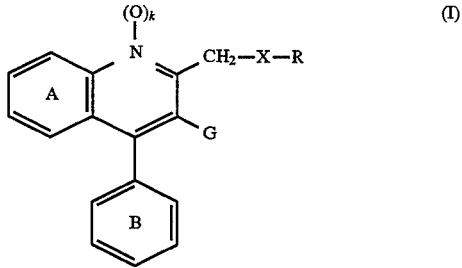

wherein
G is an acyl group, optionally protected hydroxyalkyl group, amidated carboxyl group or halogen atom;
X is an oxygen atom, optionally oxidized sulfur atom or —$(CH_2)_q$— in which q is an integer of 0 to 5;
R is an optionally substituted amino group or optionally substituted heterocyclic group;
each of the ring A and ring B may optionally be substituted; and
k is 0 or 1;
or a pharmaceutically acceptable salt thereof, and a pharmaceutically acceptable carrier.

* * * * *